(12) United States Patent
Abe et al.

(10) Patent No.: US 8,377,574 B2
(45) Date of Patent: Feb. 19, 2013

(54) DIBENZO[C,G]FLUORENE COMPOUND AND AN ORGANIC LIGHT-EMITTING DEVICE USING THE SAME

(75) Inventors: Shigemoto Abe, Tokyo (JP); Jun Kamatani, Tokyo (JP); Chiaki Nishiura, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 333 days.

(21) Appl. No.: 12/935,839

(22) PCT Filed: May 14, 2009

(86) PCT No.: PCT/JP2009/059295
§ 371 (c)(1),
(2), (4) Date: Sep. 30, 2010

(87) PCT Pub. No.: WO2009/139499
PCT Pub. Date: Nov. 19, 2009

(65) Prior Publication Data
US 2011/0042663 A1    Feb. 24, 2011

(30) Foreign Application Priority Data

May 15, 2008   (JP) .................................. 2008-127889

(51) Int. Cl.
*B32B 19/00*   (2006.01)
(52) U.S. Cl. ..... 428/690; 428/917; 313/504; 252/301.6; 564/426; 548/128; 548/131; 548/262
(58) Field of Classification Search .................. 428/690, 428/917; 313/504; 252/301.16; 564/426; 548/128, 131, 262
See application file for complete search history.

(56) References Cited

U.S. PATENT DOCUMENTS

| | | | |
|---|---|---|---|
| 6,685,524 B2 | 2/2004 | Moriyama et al. | 445/24 |
| 6,908,694 B2 | 6/2005 | Moriyama et al. | 428/690 |
| 2004/0076853 A1 | 4/2004 | Jarikov | |
| 2004/0131880 A1 | 7/2004 | Zheng et al. | |

FOREIGN PATENT DOCUMENTS

WO    03-051092 A1    6/2003

OTHER PUBLICATIONS

Wei-Zhi Wang et al., Synthesis, Photophysics, and Electroluminescence of Poly (dibenzofluorene)s, Macromolecular Rapid Communications, 2006, 27(14), pp. 1142-1148. Adachi et al., "Data book on work function or organic thin film," Database of Organic Film Work Function for Organic Electronic Device Researchers, CMC Publishing Co., 2004, pp. 36, 56, 61, 63.

*Primary Examiner* — Shane Fang
(74) *Attorney, Agent, or Firm* — Fitzpatrick, Cella, Harper & Scinto

(57) ABSTRACT

An organic light-emitting device which has high emission efficiency and high durability even at low drive voltage is provided. An organic light-emitting device including an anode, a cathode, and an organic compound layer which is interposed between the anode and the cathode, wherein the organic compound layer include at least one dibenzo[c,g] fluorene compound represented by the following General Formula (1).

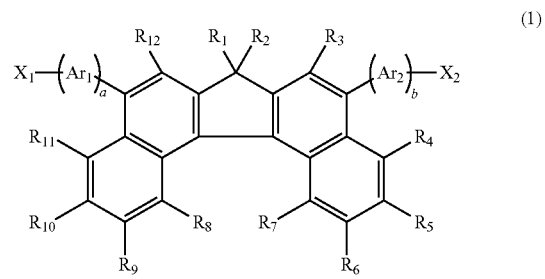

6 Claims, 3 Drawing Sheets

DIBENZO [a,h] FLUORENE

DIBENZO [a,i] FLUORENE

DIBENZO [c,g] FLUORENE

DIBENZO [a,h] FLUORENE    DIBENZO [a,i] FLUORENE

DIBENZO [c,g] FLUORENE

DIBENZO[C,G]FLUORENE COMPOUND AND AN ORGANIC LIGHT-EMITTING DEVICE USING THE SAME

TECHNICAL FIELD

The present invention relates to dibenzo[c,g]fluorene and an organic light-emitting device using the same.

BACKGROUND ART

An organic light-emitting device is an electronic device which has a thin film containing a fluorescent organic compound or a phosphorescent organic compound interposed between an anode and a cathode. In the device, holes and electrons are injected from the respective electrodes to yield excitons of the fluorescent compound or the phosphorescent compound and then light is generated from the organic light-emitting device when the excitons return to their ground state.

Recently, a significant progress has been made relating to an organic light-emitting device. The characteristic feature includes that high luminance, a variety of emission wavelengths and a high-speed response can be obtained at a low voltage and also a thin and light-weight light-emitting device can be produced. For these reason, application of an organic light-emitting device in a broad and diverse range has been suggested.

At a practical level, however, more improved luminance or higher conversion efficiency is required. In addition, there are still a lot of problems associated with durability, for example, degradation due to use for a long period of time or due to atmosphere including oxygen, moisture or the like.

Furthermore, for an application in a full-color display and the like, light emission of red, green, and blue colors with good color purity is required, but it cannot be said that such needs are completely met at the present moment.

To solve the above described problems, a dibenzo[c,g]fluorene compound has been proposed as a constitutional material for an organic light-emitting device. For example, International Publication WO2003/051092, U.S. Patent Application Publication No. 2004/0131880, and Wei-Zhi Wang et. al., "Synthesis, photophysics, and electroluminescence of poly(dibenzo fluorene)s", Macromolecular Rapid Communications Vol. 27, No. 14, p. 1142 (2006), can be mentioned in which a dibenzo[c,g]fluorene compound or an organic light-emitting device using a dibenzo[c,g]fluorene compound as a constitutional material is described.

The dibenzo[c,g]fluorene compound disclosed in International Publication WO2003/051092 is substituted at 5-position and 9-position with a heterocyclic group with hole transporting property such as an oxadiazole group, a thiadiazole group, a triazole group, a diarylamine group, and a carbazole group.

In addition, the dibenzo[c,g]fluorene compound disclosed in U.S. Patent Application Publication No. 2004/0131880 is also substituted at 5-position and 9-position with a heterocyclic group such as a thiophene group, and a carbazole group.

Incidentally, according to the literature by Wei-Zhi Wang et. al. ("Synthesis, photophysics, and electroluminescence of poly(dibenzo fluorene)s", Macromolecular Rapid Communications. Vol. 27, No. 14, p. 1142 (2006)), the characteristics of an organic light-emitting device in which a polymer having a dibenzo[c,g]fluorene skeleton is used as a constitutional material are described. However, it cannot be said that the characteristics exhibited as a polymer material are necessarily reflected as they are on a low molecular weight material. That is because, as having a molecular weight distribution contrary to a low molecular weight material, the polymer material is a mixture containing many compounds having various molecular weights and at the same time is a material which has an energy distribution with a certain range. Therefore, for example, the light-emitting behavior of a polymer material is basically different from the light-emitting behavior of a low molecular weight material.

DISCLOSURE OF THE INVENTION

An object of the present invention is to provide a dibenzo[c,g]fluorene compound which is mainly used as a material for an organic light-emitting device. In addition, another object of the present invention is to provide an organic light-emitting device which has favorable emission efficiency at a low voltage and high durability. Thus, according to the present invention, a dibenzo[c,g]fluorene compound that is represented by the following General Formula (1) is provided.

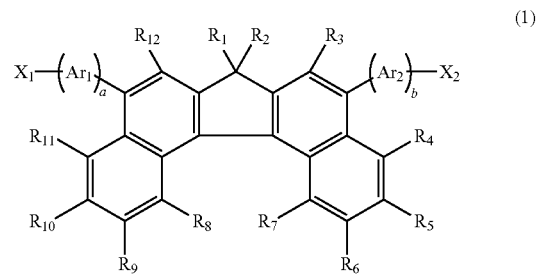

(1)

In General Formula (1), $X_1$ and $X_2$ each represent a hydrogen atom, a substituted or unsubstituted aryl group or a substituted or unsubstituted alkyl group and may be the same or different, $Ar_1$ and $Ar_2$ each represent a substituted or unsubstituted arylene group and may be the same or different, $R_1$, $R_2$, $R_3$, $R_4$, $R_5$, $R_6$, $R_7$, $R_8$, $R_9$, $R_{10}$, $R_{11}$, and $R_{12}$ each represent a hydrogen atom, a substituted or unsubstituted alkyl group and may be the same or different, and a and b each represent an integer of 0 to 3, provided that a+b is 1 or more and 4 or less, and when a is 2 or more, $Ar_1$'s may be the same or different and when b is 2 or more, $Ar_2$'s may be the same or different.

According to the present invention, a dibenzo[c,g]fluorene compound which is mainly used as a material for an organic light-emitting device is provided. In addition, according to the present invention, an organic light-emitting device which has favorable emission efficiency at a low voltage and high durability is provided.

Further features of the present invention will become apparent from the following description of exemplary embodiments with reference to the accompanying drawings.

BEST MODE FOR CARRYING OUT THE INVENTION

Figure 1:
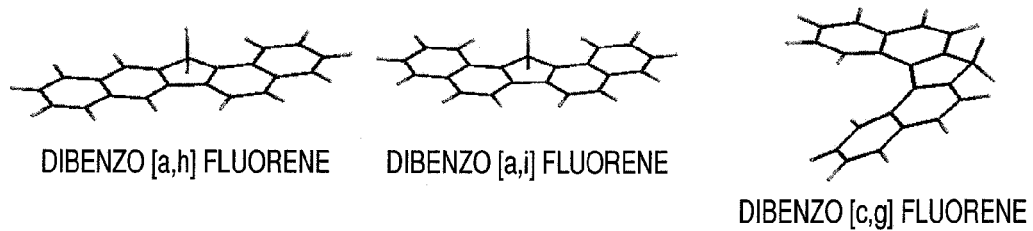
FIG. 1 is a graphic showing steric structures of a dibenzo[c,g]fluorene compound and isomers thereof.

Preferred embodiments of the present invention will now be described in detail in accordance with the accompanying drawings.

First, the dibenzo[c,g]fluorene compound of the present invention will be explained in detail.

The dibenzo[c,g]fluorene compound of the present invention is a compound which is represented by the following General Formula (1).

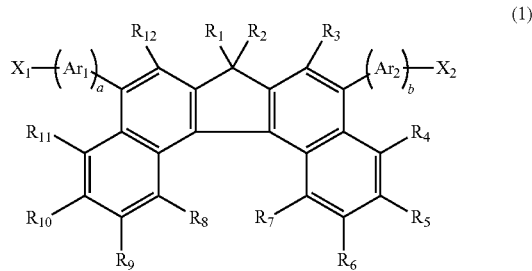

(1)

In the General Formula (1), $X_1$ and $X_2$ each represent a hydrogen atom, a substituted for unsubstituted aryl group, or a substituted or unsubstituted alkyl group.

Examples of the aryl group represented by $X_1$ or $X_2$ may include, but are not limited to a phenyl group, a naphthyl group, an azurenyl group, an acenaphthylenyl group, an indacenyl group, a biphenylenyl group, a fluorenyl group, an anthrolyl group, a phenanthryl group, a pyrenyl group, a chrysenyl group, a benzofluorenyl group, a tetraphenyl group, a naphthacenyl group, a triphenylenyl group, a fluoranthenyl group, a picenyl group, a pentacenyl group, a perylenyl group, a benzofluoranthenyl group, and a naphthofluoranthenyl group.

Examples of the alkyl group represented by $X_1$ or $X_2$ may include, but are not limited to a methyl group, an ethyl group, a n-propyl group, an iso-propyl group, a n-butyl group, an iso-butyl group, a sec-butyl group, a tert-butyl group, a n-pentyl group, a neo pentyl group, a n-hexyl group, a n-octyl group, a n-decyl group, a n-dodecyl group, a cyclopropyl group, a cyclobutyl group, a cyclopentyl group, a cyclohexyl group, a norbornyl group, and an adamantyl group.

Examples of the substituent which may be included in the aryl group or the alkyl group as described above may include, but are not limited to, an alkyl group such as a methyl group, an ethyl group, a propyl group, a tert-butyl group, an iso-butyl group, a sec-butyl group, and a tert-butyl group, and an aryl group such as a phenyl group, a terphenyl group, a naphthyl group, a biphenyl group, a fluorenyl group, 9,9-dimethyl fluorenyl group, a phenanthryl group, and a chrysenyl group.

Incidentally, $X_1$ and $X_2$ may be the same or different from each other.

$Ar_1$ and $Ar_e$ each represent a substituted or unsubstituted arylene group.

Examples of the arylene group represented by $Ar_1$ or $Ar_2$ include, but are not limited to, a phenylene group, a naphthylene group, an azurenylene group, an acenaphthylenylene group, an indacenylene group, a biphenylene group, a terphenylene group, a fluorenylene group, an anthrylene group, a phenanthrylene group, a pyrenylene group, a chrysenylene group, a benzofluorenylene group, a tetraphenylene group, a naphthacenylene group, a triphenylene group, a fluoranthenylene group, a picenylene group, a pentacenylene group, a perylenylene group, a benzofluoranthenylene group, a naphthofluoranthenylene group, a divalent substituent which is derived from the fused ring described below.

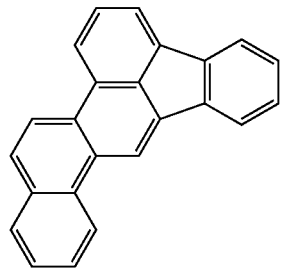 [SMILES: c1ccc2c(c1)-c1cccc3c1c-2cc1c2ccccc2ccc31]

With respect to the arylene group represented by $Ar_1$ or $Ar_2$, preferred is a substituent selected from the group consisting of a phenylene group, a biphenylene group, a terphenylene group, a naphthylene group, an anthrylene group, a phenanthrylene group, a pyrenylene group and a fluorenylene group.

Examples of the substituent which may be included in the arylene group as described above include, but are not limited to, an alkyl group such as a methyl group, an ethyl group, propyl group, a tert-butyl group, an iso-butyl group, a sec-butyl group, and a tert-butyl group, and an aryl group such as a phenyl group, a terphenyl group, a naphthyl group, a biphenyl group, a fluorenyl group, 9,9-dimethyl fluorenyl group, a phenanthryl group, and a chrysenyl group.

$Ar_1$ and $Ar_2$ may be the same or different from each other.

$R_1$ to $R_{12}$ represent respectively a hydrogen atom, a substituted or unsubstituted alkyl group.

With respect to an alkyl group represented as $R_1$ to $R_{12}$, examples include a methyl group, an ethyl group, a n-propyl group, an iso-propyl group, a n-butyl group, an iso-butyl group, a sec-butyl group, a tert-butyl group, a n-pentyl group, a neo pentyl group, a n-hexyl group, a n-octyl group, a n-decyl group, a n-dodecyl group, a cyclopropyl group, a cyclobutyl group, a cyclopentyl group, a cyclohexyl group, a norbornyl group, an adamantyl group and the like, but clearly not limited thereto.

With respect to a substituent which may be included in an alkyl group as described above, examples include an alkyl group such as a methyl group, an ethyl group, propyl group, a tert-butyl group, an iso-butyl group, a sec-butyl group, and a tert-butyl group, and an aryl group such as a phenyl group, a terphenyl group, a naphthyl group, a biphenyl group, a fluorenyl group, a phenanthryl group, and a chrysenyl group, but clearly not limited thereto.

$R_1, R_2, R_3, R_4, R_5, R_6, R_7, R_8, R_9, R_{10}, R_{11}$, and $R_{12}$ may be the same or different from each other.

a and b each represent an integer of 0 to 3, provided that a+b is 1 or more and 4 or less.

When a is 2 or more, $Ar_1$'s may be the same or different from each other.

When b is 2 or more, $Ar_2$'s may be the same or different from each other.

Regarding the dibenzo[c,g]fluorene compound of the present invention, also preferred aspect is a compound of General Formula (1) in which a represents 0 and $X_1$ represents a hydrogen atom or a substituted or unsubstituted alkyl group.

Next, a method of synthesizing the dibenzo[c,g]fluorene compound of the present invention will be described.

Specifically, the dibenzo[c,g]fluorene compound of the present invention can be synthesized by carrying out the steps (I) and (II) described below.

(I) Synthesis of halogenated product or boronic acid derivative of dibenzo[c,g]fluorene (II) Synthesis of dibenzo[c,g]fluorene compound from halogenated product or boronic acid derivative synthesized in step (I) utilizing coupling reaction First, the step (I) will be described. A bromine-substituted dibenzo[c,g]fluorene compound can be synthesized via the method as shown in following Scheme 1.

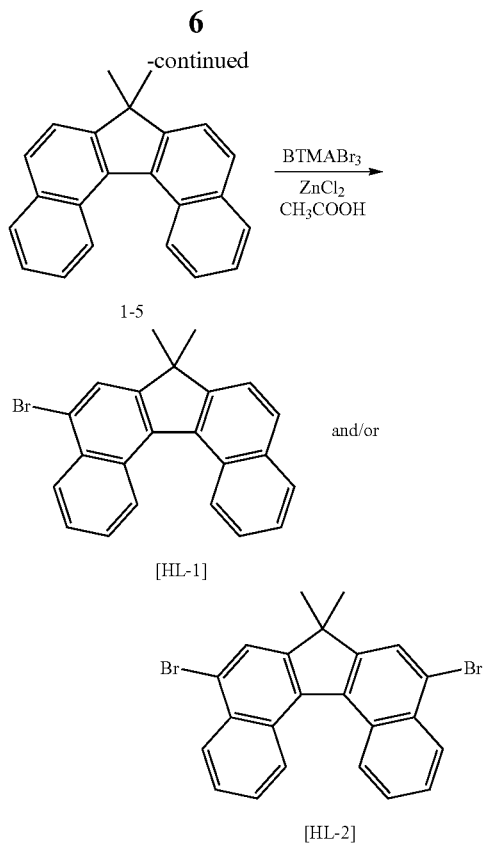

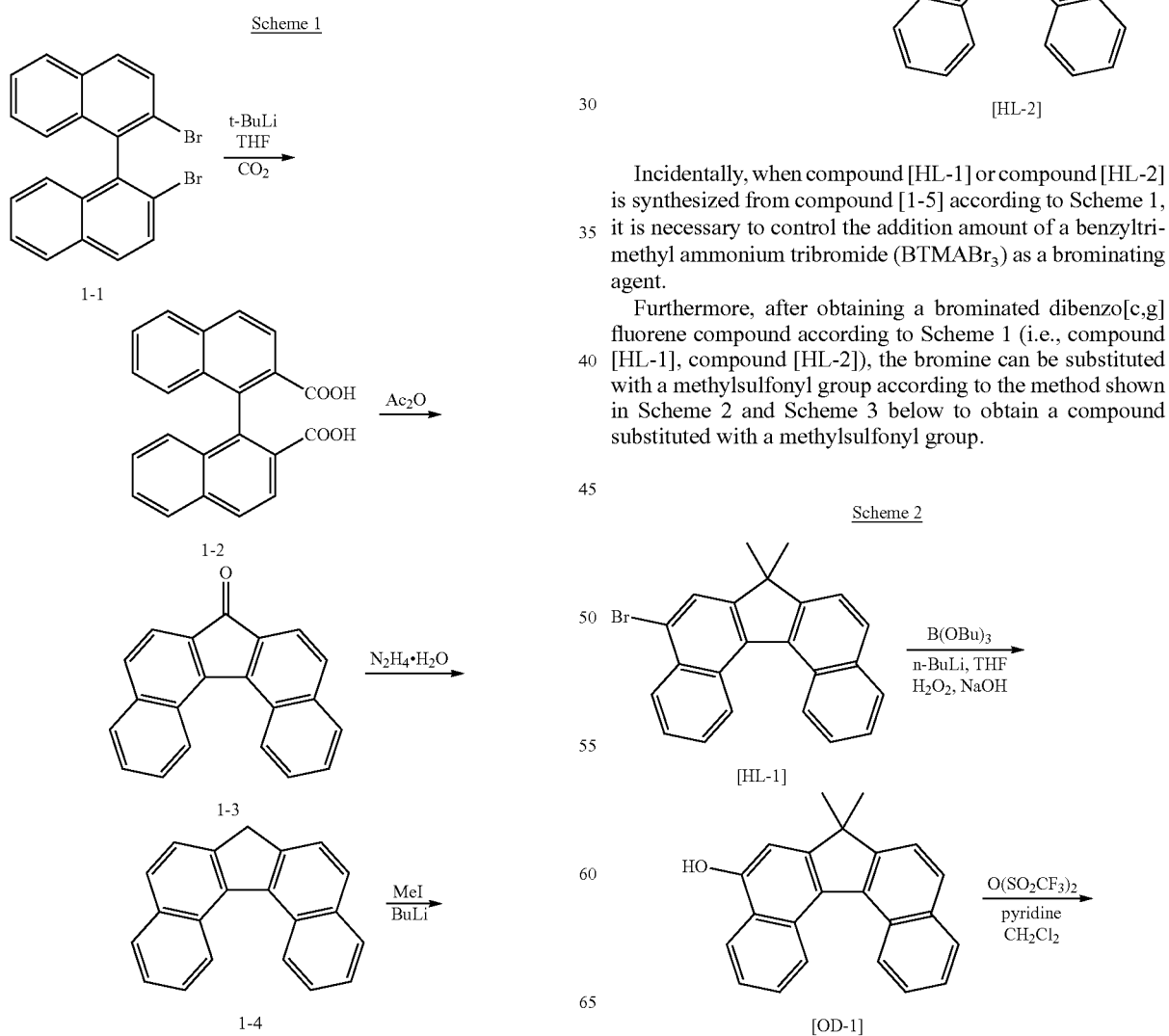

Incidentally, when compound [HL-1] or compound [HL-2] is synthesized from compound [1-5] according to Scheme 1, it is necessary to control the addition amount of a benzyltrimethyl ammonium tribromide ($BTMABr_3$) as a brominating agent.

Furthermore, after obtaining a brominated dibenzo[c,g] fluorene compound according to Scheme 1 (i.e., compound [HL-1], compound [HL-2]), the bromine can be substituted with a methylsulfonyl group according to the method shown in Scheme 2 and Scheme 3 below to obtain a compound substituted with a methylsulfonyl group.

-continued

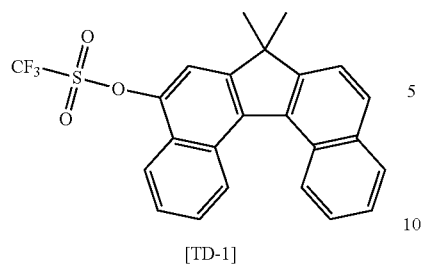

[TD-1]

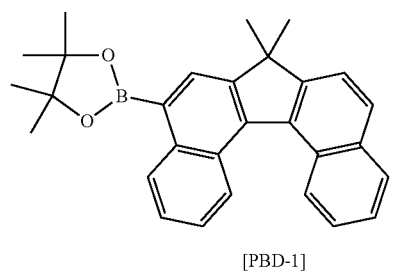

[PBD-1]

Scheme 3

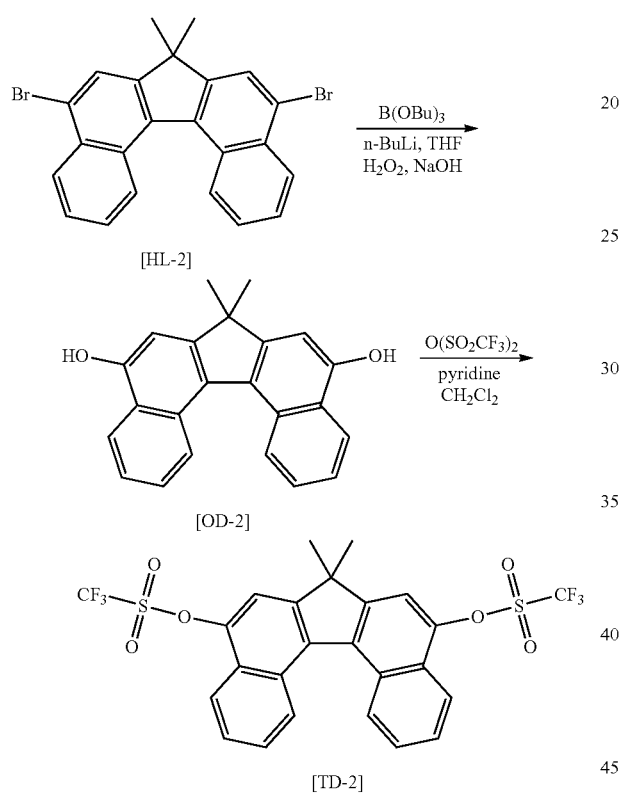

[HL-2] → [OD-2] → [TD-2]

On the other hand, compound [PBD-1] or compound [PBD-2] as a boronic acid ester derivative can be synthesized from the bromine-substituted compound [HL-1] or compound [HL-2] according to the method shown in Schemes 4 and 5.

Scheme 4

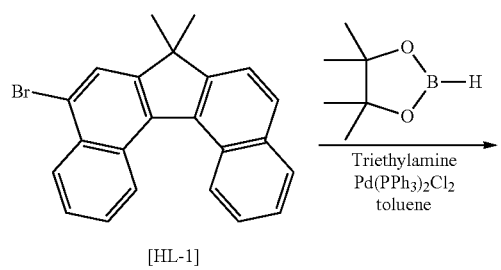

[HL-1]

Scheme 5

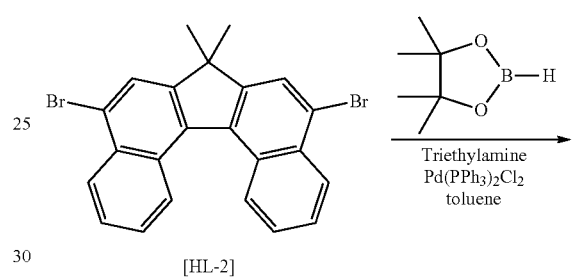

[HL-2]

[PBD-2]

Furthermore, instead of synthesizing a boronic acid ester derivative, compound [BAD-1] or compound [BAD-2] as a boronic acid derivative can be synthesized from the bromine-substituted compound [HL-1] or compound [HL-2] according to the method shown in Schemes 6 and 7.

Scheme 6

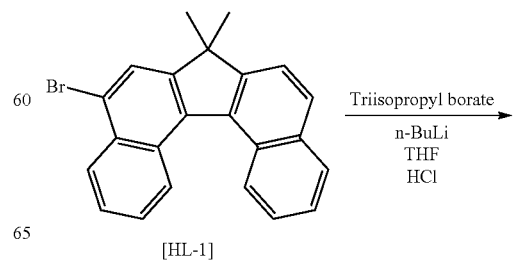

[HL-1]

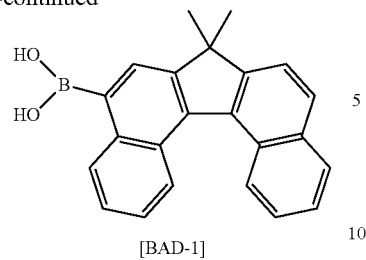

[BAD-1]

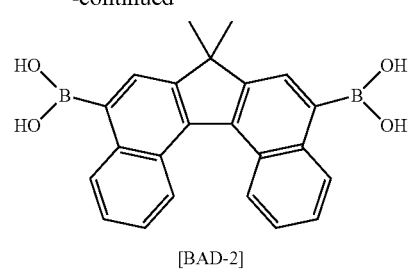

[BAD-2]

Next, the step (II) will be described. For carrying out the step (II), as the combination for a coupling reaction, a combination of the above described bromine-substituted compound or methylsulfonyl group substituted compound and the above described boronic acid ester derivative or boronic acid derivative can be mentioned.

Herein below, specific examples of a coupling reaction will be described.

As a first example, combination of a bromine-substituted compound and a boronic acid ester derivative or a boronic acid derivative as shown in Schemes 8 to 10 can be mentioned.

Scheme 7

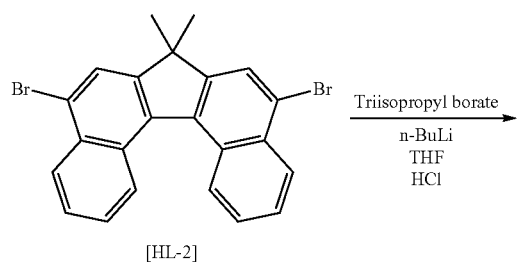

[HL-2]

Scheme 8

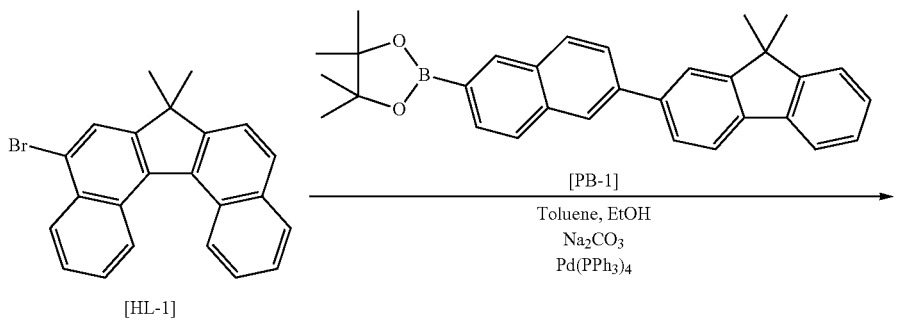

[HL-1]

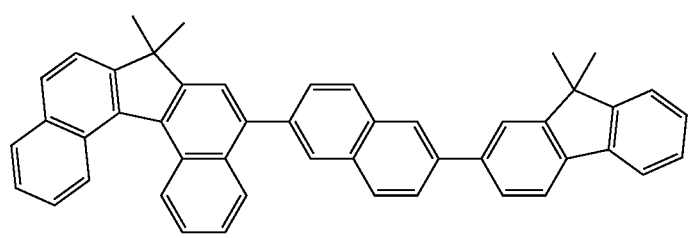

Scheme 9

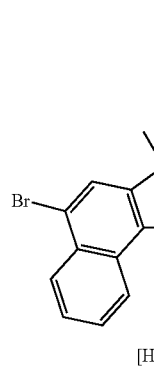
[HL-2]

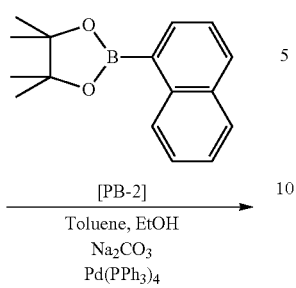
[PB-2]

→ Toluene, EtOH, Na₂CO₃, Pd(PPh₃)₄

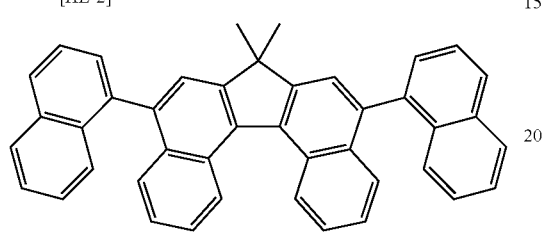

Scheme 10

[HL-2]

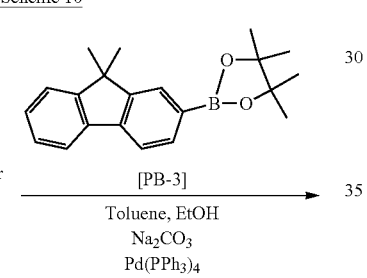
[PB-3]

→ Toluene, EtOH, Na₂CO₃, Pd(PPh₃)₄

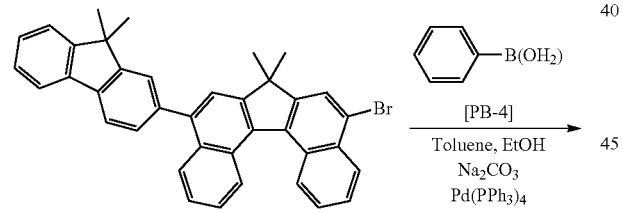
[HLI]

Ph—B(OH)₂ [PB-4]

→ Toluene, EtOH, Na₂CO₃, Pd(PPh₃)₄

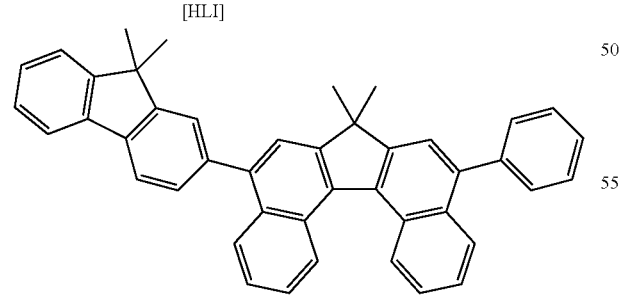

In this case, however, a boronic acid ester derivative and a boronic acid derivative used for carrying out the coupling reaction as shown in the above described Scheme 8 are not limited to the above [PB-1]. For example, a boronic acid ester derivative and a boronic acid derivative that are exemplified in Table 1 below can be also used.

TABLE 1

Compound which can be used instead of [PB-1]

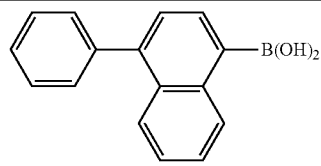

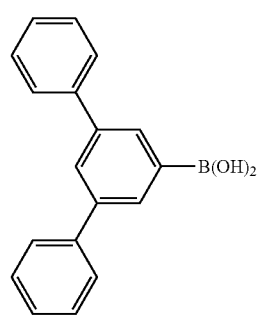 [SMILES: OB(O)c1cc(-c2ccccc2)cc(-c2ccccc2)c1]

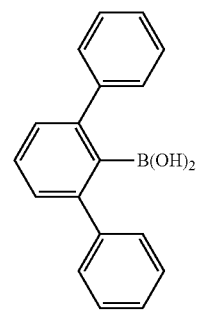 [SMILES: OB(O)c1c(-c2ccccc2)cccc1-c1ccccc1]

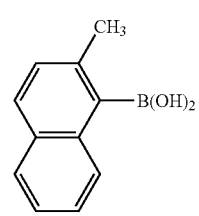

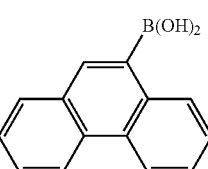

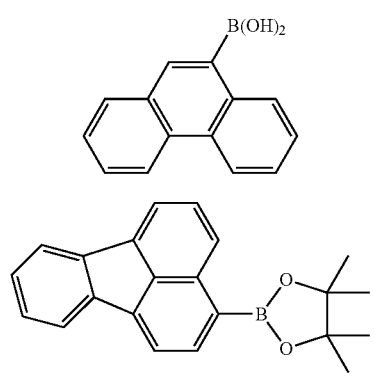

TABLE 1-continued

Compound which can be used instead of [PB-1]

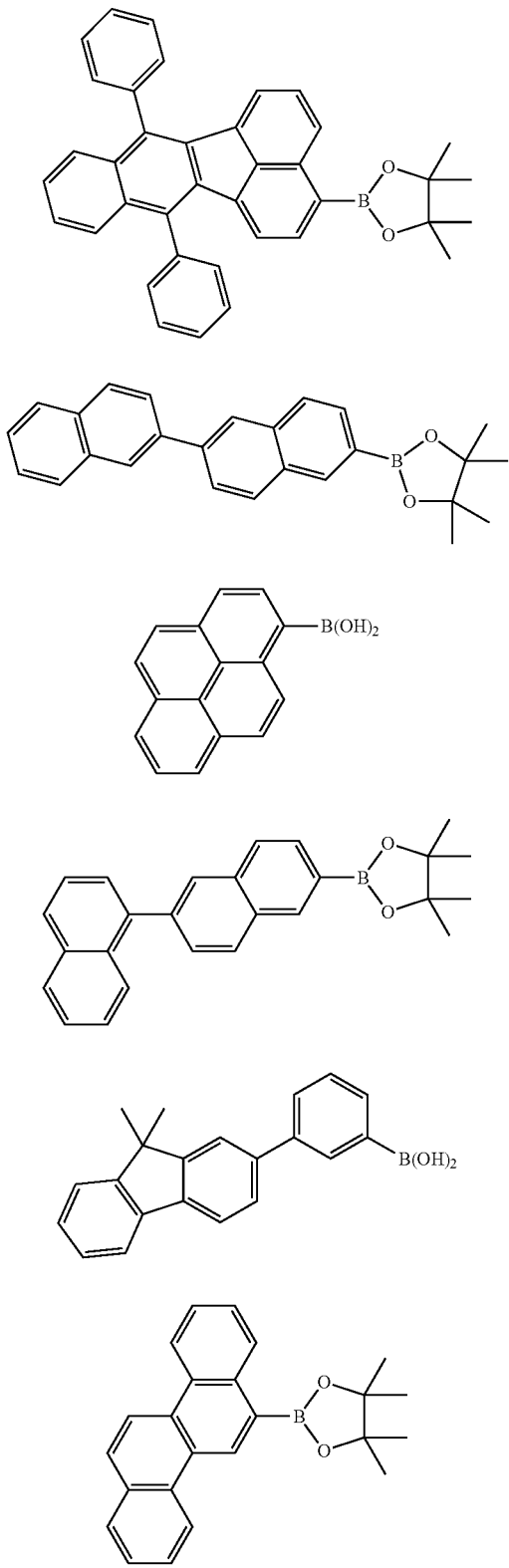

TABLE 1-continued

Compound which can be used instead of [PB-1]

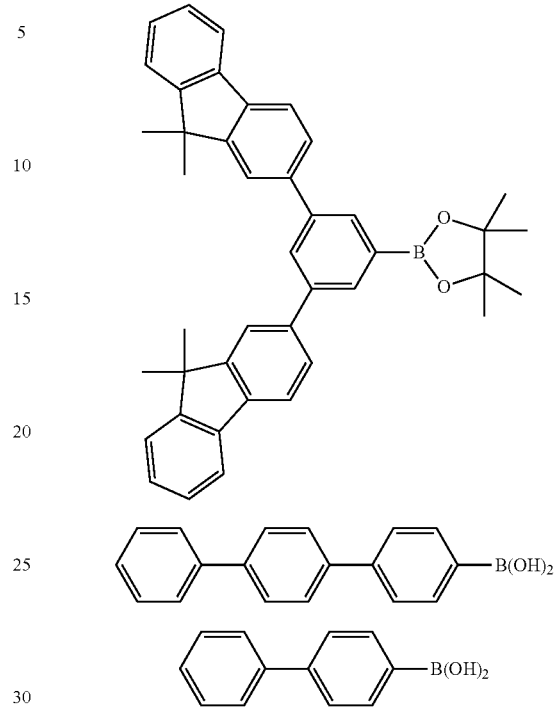

Furthermore, a boronic acid ester derivative and a boronic acid derivative used for carrying out the coupling reaction as shown in the above described Scheme 9 are not limited to the above [PB-2]. For example, a boronic acid ester derivative and a boronic acid derivative that are exemplified in Table 2 below can be also used.

TABLE 2

Compound which can be used instead of [PB-2]

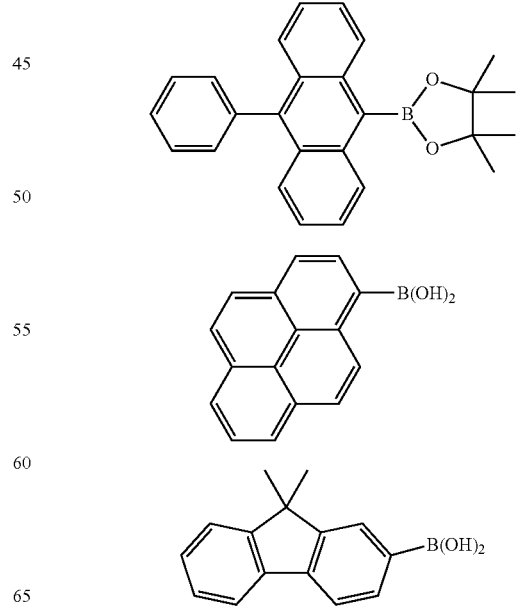

TABLE 2-continued

Compound which can be used instead of [PB-2]

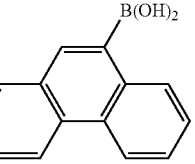

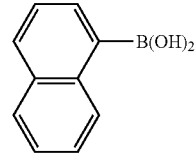 [SMILES: OB(O)c1cccc2ccccc12]

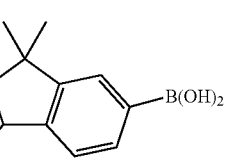

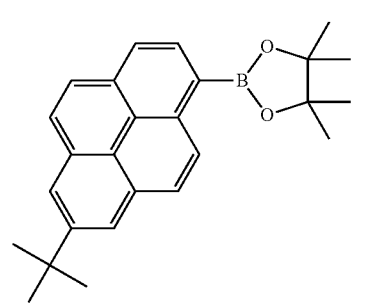 [SMILES: CC(C)(C)c1cc2ccc3ccc(B4OC(C)(C)C(C)(C)O4)c4ccc(c1)c2c34]

Still further, a boronic acid ester derivative and a boronic acid derivative used for carrying out the coupling reaction as shown in the above described Scheme 10 are not limited to the above [PB-3] and [PB-4]. For example, a boronic acid ester derivative and a boronic acid derivative that are exemplified in Table 3 below can be also used.

TABLE 3

| Compound which can be used instead of [PB-3] | Compound which can be used instead of [PB-4] |
|---|---|
| 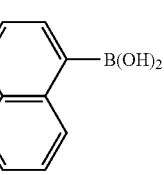 | 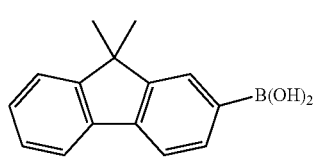 [SMILES: CC1(C)c2ccccc2-c2ccc(B(O)O)cc21] |
| | 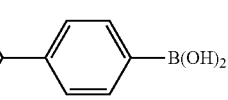 |
| 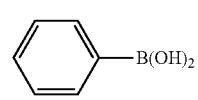 | |
| | 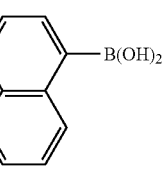 |
| | |
| 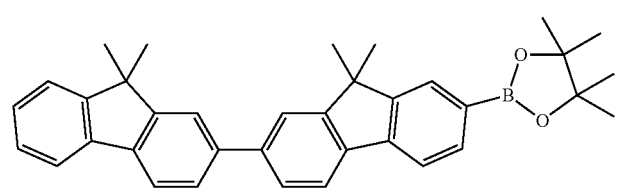 [SMILES: CC1(C)c2ccccc2-c2ccc(-c3ccc4c(c3)C(C)(C)c3cc(B5OC(C)(C)C(C)(C)O5)ccc3-4)cc21] | |

As a second example, the combination of a boronic acid ester derivative and a methylsulfonyl group substituted compound or a halogenated compound as shown in Schemes 11 to 13 can be mentioned.
Scheme 11
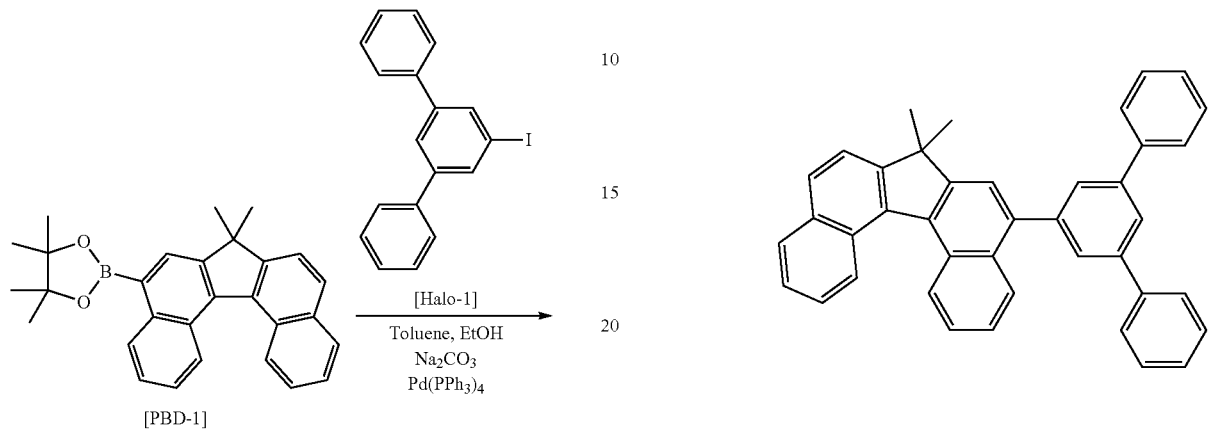
Scheme 12
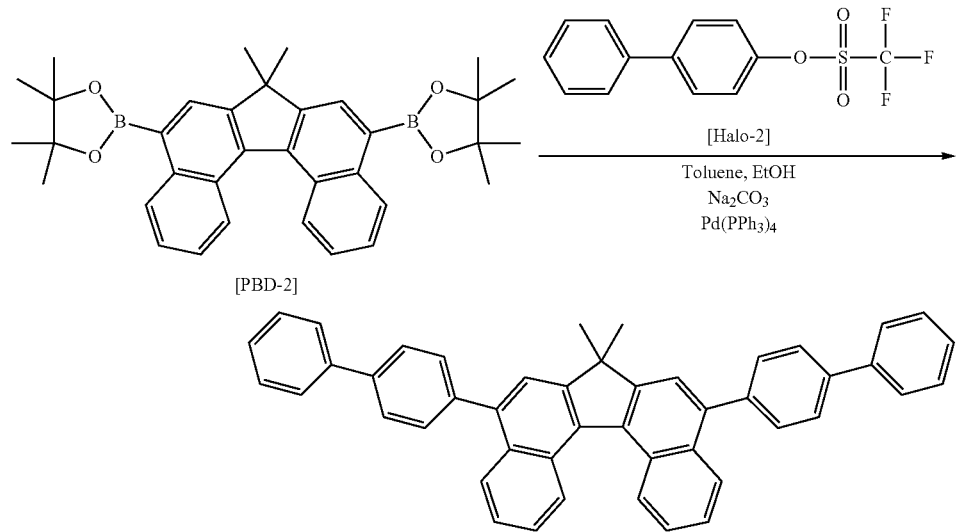
Scheme 13
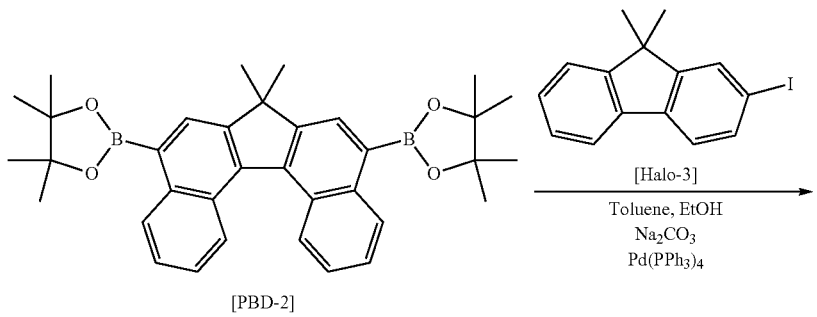

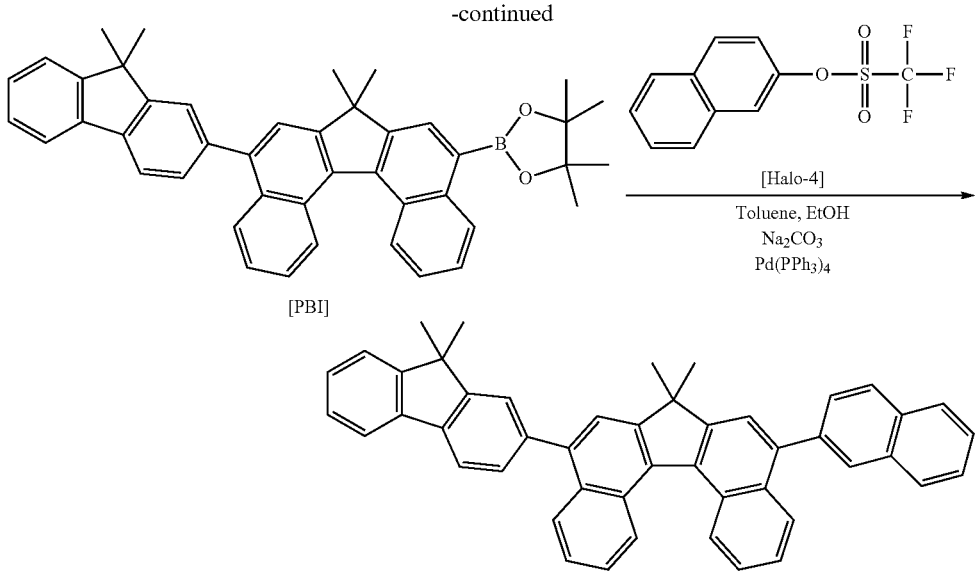

In this case, however, a methylsulfonyl group substituted compound and a halogenated compound used for carrying out the coupling reaction as shown in the above described Scheme 11 are not limited to the above [Halo-1]. For example, a methylsulfonyl group substituted compound and a halogenated compound that are exemplified in Table 4 below can be also used.

TABLE 4

Compound which can be used instead of [Halo-1]

TABLE 4-continued

Compound which can be used instead of [Halo-1]

Furthermore, a methylsulfonyl group substituted compound and a halogenated compound used for carrying out the coupling reaction as shown in the above described Scheme 12 are not limited to the above [Halo-2]. For example, a methylsulfonyl group substituted compound and a halogenated compound that are exemplified in Table 5 below can be also used.

TABLE 5

Compound which can be used instead of [Halo-2]

TABLE 5-continued

Compound which can be used instead of [Halo-2]

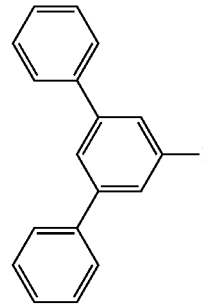

Still further, a methylsulfonyl group substituted compound and a halogenated compound used for carrying out the coupling reaction as shown in the above described Scheme 13 are not limited to the above [Halo-3] and [Halo-4]. For example, a methylsulfonyl group substituted compound and a halogenated compound that are exemplified in Table 6 below can be also used.

TABLE 6

| Compound which can be used instead of [Halo-3] | Compound which can be used instead of [Halo-4] |
|---|---|

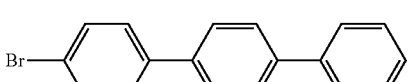

TABLE 6-continued

| Compound which can be used instead of [Halo-3] | Compound which can be used instead of [Halo-4] |
|---|---|
| (9,9-dimethylfluorene with I substituent) | (fluoranthene with Br substituent) |

The dibenzo[c,g]fluorene compound of the present invention has an aryl group which consists of only hydrocarbon. By having an aryl group as a substituent which consists of only hydrocarbon, the dibenzo[c,g]fluorene compound of the present invention has better emission efficiency and durability compared to a dibenzo[c,g]fluorene compound having a substituent such as a heterocyclic group which includes a hetero atom.

Incidentally, as one factor which can cause emission degradation due to energization, disruption in balance (carrier balance) between hole current and electron current within a light-emitting layer (hereinafter, sometimes simply referred to as "emission layer") can be considered. For the amount of carrier injected into a light-emitting layer and the amount of carrier transported in the light-emitting layer, when there is a significant difference between the both carriers, an area in which the both carriers are recombined with each will be concentrated in an interface region between the light-emitting layer and a carrier transport layer, resulting in localization of a light-emitting area. If the light-emitting area is localized, carriers will be accumulated in a region near the interface between the light-emitting layer and the carrier transport layer when energized for a long period of time. As a result, because the molecular structure of an emission center material or neighboring molecules thereof will become susceptible to material degradation, there is a large possibility that emission degradation may be caused.

As one factor which may cause disruption in carrier balance within a light-emitting layer, in addition to a difference in carrier transporting property of a material constituting a light-emitting layer as described above, impurities which are contained in such constituting materials and behave as a carrier trap can be mentioned.

In general, a substituent such as a heterocyclic group which includes a hetero atom is a substituent in which carbon atom (s) of an aryl group skeleton is substituted with nitrogen atom(s) or oxygen atom(s), both having high polarity. Thus, a substituent which includes a hetero atom is more polar than an aryl group which consists of only hydrocarbon, and therefore it can easily incorporate an ionic impurity compared to an aryl group. For such reasons, as a material for light emission, it is better to use a compound substituted with an aryl group which consists of hydrocarbon only instead of a heterocyclic group, to remove any factor which can introduce degradation of a device caused by ionic impurities. As a result, a longer lifetime of a device can be obtained.

In addition, a substituent such as a heterocyclic group including a hetero atom has electron donating property or electron withdrawing property higher than that of an aryl group. Thus, compared to a compound substituted only with an aryl group, it has significantly higher or lower HOMO value of a molecule. Table 7 shown below includes a summary of HOMO values of various compounds used as a material constituting an organic light-emitting device. Incidentally, each of the HOMO values is obtained from the "Database of Organic Film Work Function for Organic Electronic Device Researchers" (Chihaya Adachi, Takahito Oyamada, Yoshiyuki Nakajima, CMC Publishing Co. 2004).

TABLE 7

| Heteroatom containing Compound (including heterocyclic compound) | HOMO |
|---|---|
| (phenyl-thiophene-phenylene-thiophene-phenyl compound) | 5.3 eV |
| (2,4,6-tri(2-pyridyl)-1,3,5-triazine) | 5.2 eV |
| (N,N,N',N'-tetra(p-tolyl)benzidine) | 5.3 eV |
| (thiophene-quinoline diphenyl compound) | 6.2 eV |

TABLE 7-continued

| Heteroatom containing Compound (including heterocyclic compound) | HOMO |
|---|---|
| [structure: pyrazine with two diphenyl-thiophene substituents] | 6.0 eV |
| [structure: triazine with three carbazole substituents] | 6.0 eV |

Incidentally, when LUMO level of a material which constitutes a light-emitting layer is close to HOMO level of a material which constitutes a hole transport layer, at the interface, an energy band which is smaller than the original energy band of the material which constitutes the light-emitting layer is formed, so that excimer light emission can easily occur. Similarly, when HOMO level of the material which constitutes the light-emitting layer is close to LUMO level of a material which constitutes an electron transport layer, excimer light emission can also easily occur. Thus, when an organic compound having a substituent such as a heterocyclic group containing a hetero atom, wherein HOMO level and LUMO level of a molecule itself become significantly high or low, is used as the material for constituting the light-emitting layer, an excimer can be easily formed with a material which constitutes a neighboring hole transport layer, an electron transport layer, or the like. Once an excimer is formed, not only emission efficiency is lowered but also emission color of a device becomes difficult to control due to a shift of emission wavelength to a longer wavelength side. Taken all together, like the dibenzo[c,g]fluorene compound of the present invention, by substituting the dibenzo[c,g]fluorene compound skeleton with an aryl group consisting of only hydrocarbon instead with a group containing a hetero atom such as a heterocyclic group, the emission efficiency of a device can be improved.

Moreover, the aryl group which can be substituted on the skeleton of a dibenzo[c,g]fluorene compound is not specifically limited. However, when the compound is purified by sublimation or a thin film is formed by an evaporation process or the like, it is preferable that the aryl group is a substituent in which at most four benzene rings are linked or a fused ring group in which at most four rings are fused. Examples thereof include an aryl group selected from the group consisting of a phenyl group, a biphenyl group, a terphenyl group, a naphthyl group, an anthryl group, a phenanthryl group, a pyrenyl group, and a fluorenyl group.

Meanwhile, dibenzo[c,g]fluorene has a characteristic steric structure compared to other isomers of dibenzofluorene compound. FIG. 1 shows steric structures of dibenzo[c,g]fluorene and its isomer. Incidentally, the steric structures are calculated based on Chem3D Ultra. As shown in FIG. 1, in the dibenzo[c,g]fluorene compound of the present invention, the hydrogen at 1-position and the hydrogen at 13-position repel each other, resulting in deformation of the skeleton of dibenzofluorene itself. As a result, the molecule becomes to have a spiral structure as a whole. On the other hand, dibenzo[a,h]fluorene and dibenzo[a,i]fluorene as the isomers each have a planar structure.

If a molecule has a planar structure having a large conjugation plane, not only amorphous property of a material is lowered but also emission efficiency is lowered when used at high concentration as a light-emitting material. Basic reason for such phenomenon can be explained, for example, with pyrene, which is a representative compound having a planar structure. Pyrene has been studied for a long period of time as a blue light emitting material, and at a high concentration it is known to have excimer emission in addition to monomer light emission. This is because, if a bulky substituent which can cause a steric hindrance on a pyrene skeleton is not introduced, pyrene molecules can form a stack structure by themselves to generate an energy band having smaller energy than the original energy band. As a result, the emission light is shifted to a longer wavelength side and at the same time the emission efficiency is lowered.

Thus, the dibenzo[c,g]fluorene compound of the present invention, which is impossible to have a planar structure, has higher amorphous property compared to other dibenzofluorene compounds having a planar structure, and also an intermolecular stack can be inhibited. As a result, excimer light emission can be inhibited. Furthermore, the dibenzo[c,g]fluorene compound of the present invention which has high amorphous property and is capable of inhibiting an intermolecular stack can also inhibit concentration quenching when used as a dopant. Thus, the emission efficiency can be improved.

Furthermore, from a molecular orbital calculation, it was found that the dibenzo[c,g]fluorene compound of the present invention has relatively shallow HOMO compared to other hydrocarbon aromatic compounds. In the following Table 8, HOMO and LUMO values that are measured and calculated for a compound having a dibenzo[c,g]fluorene skeleton and for a compound not having such skeleton are enumerated. Incidentally, each of the measured values of HOMO is obtained by using a photoelectron spectroscope AC-2 (manufactured by Riken Keiki Co., LTD). In addition, each of the measured values of LUMO is obtained from a band gap determined from a Ultraviolet-visible spectrophotometer.

TABLE 8

| | Measured value | | Calculated result | |
|---|---|---|---|---|
| | HOMO [eV] | LUMO [eV] | HOMO [eV] | LUMO [eV] |
| (structure 1) | 5.67 | 2.79 | −5.15 | −1.55 |
| (structure 2) | 5.83 | 2.74 | −5.36 | −1.34 |
| (structure 3) | 5.69 | 2.80 | −5.20 | −1.55 |
| (structure 4) | 5.92 | 2.90 | −5.45 | −1.41 |

Meanwhile, as the HOMO level of a material which constitutes a light-emitting layer is deeper compared to the HOMO level of a material which constitutes a hole transport/injection layer, the hole injection barrier from a hole transport/injection layer to the light-emitting layer becomes higher.

When the hole injection barrier becomes higher, it is easier for a carrier to get accumulated near an interface between a light-emitting layer and a hole transport/injection layer and the drive voltage is also increased. As a result, a light emission area may be localized near an interface between a light-emitting layer and a hole transport/injection layer. In particular, when HOMO level of a guest included in the light-emitting layer is shallower than the HOMO level of a host included in the light-emitting layer and the difference between them is large, the hole trapping property within the light-emitting layer increases, thereby making the above-mentioned phenomenon (carrier accumulation phenomenon) significant.

In this case, if the dibenzo[c,g]fluorene compound of the present invention is used as a host for a light-emitting layer, a hole injection barrier from a hole transport/injection layer to a light-emitting layer is lowered because the compound itself has a shallow HOMO level. As a result, a hole injectability to the light-emitting layer is improved so that the reduction of drive voltage can be achieved. It is considered that, when the hole injection barrier is lowered, the carrier balance is also improved and the light emission region is enlarged. Furthermore, if it is combined with a guest molecule having a deeper LUMO level, the hole trapping property within the light-emitting layer is lowered so that the carrier balance is more improved and the light emission region is more enlarged, thus it is expected that a device can have longer lifetime and higher efficiency.

As described above, the dibenzo[c,g]fluorene compound of the present invention has a suitably shallow HOMO, thus producing no excimer with a material which constitutes a neighboring hole transport layer, an electron transport layer, or the like, and also, it becomes possible that the hole injection barrier from the hole transport/injection layer to the light-emitting layer is lowered.

Meanwhile, the dibenzo[c,g]fluorene compound of the present invention can be classified into three major groups depending on the substituent present on the skeleton of the dibenzo[c,g]fluorene compound and the position of such substituent.

(A) Same kind of an aryl group is substituted on 5-position and 9-position of the skeleton of a dibenzo[c,g]fluorene compound. Herein below, it is designated as compound group [SY].

Compound group [SY]

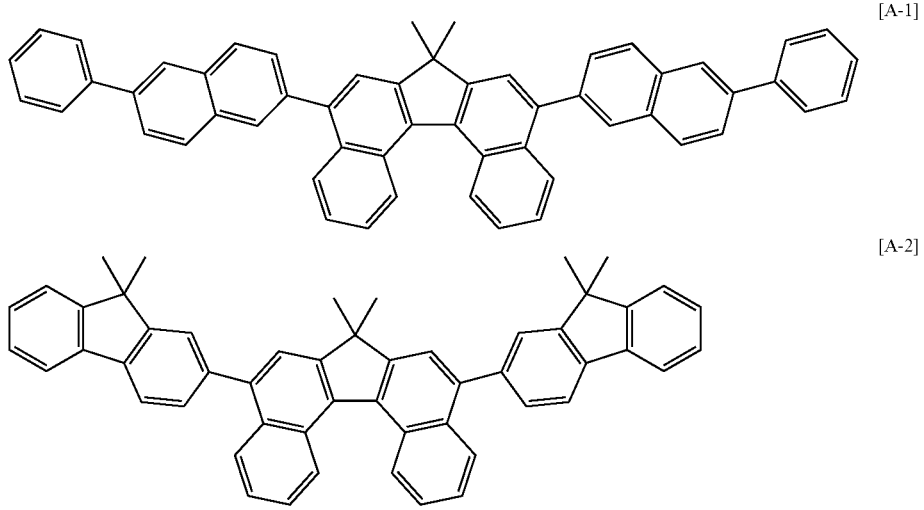

Having high symmetry in molecular structure and high crystallinity, the compound group [SY] has high carrier mobility. Thus, when the compound group [SY] is used as a host for a light-emitting layer, the carriers of both holes and electrons can be efficiently transported, and therefore the drive voltage for a device can be reduced.

(B) Different kinds of aryl groups are substituted on 5-position and 9-position of the skeleton of a dibenzo[c,g]fluorene compound. Herein below, it is designated as compound group [AS].

Compound group [AS]

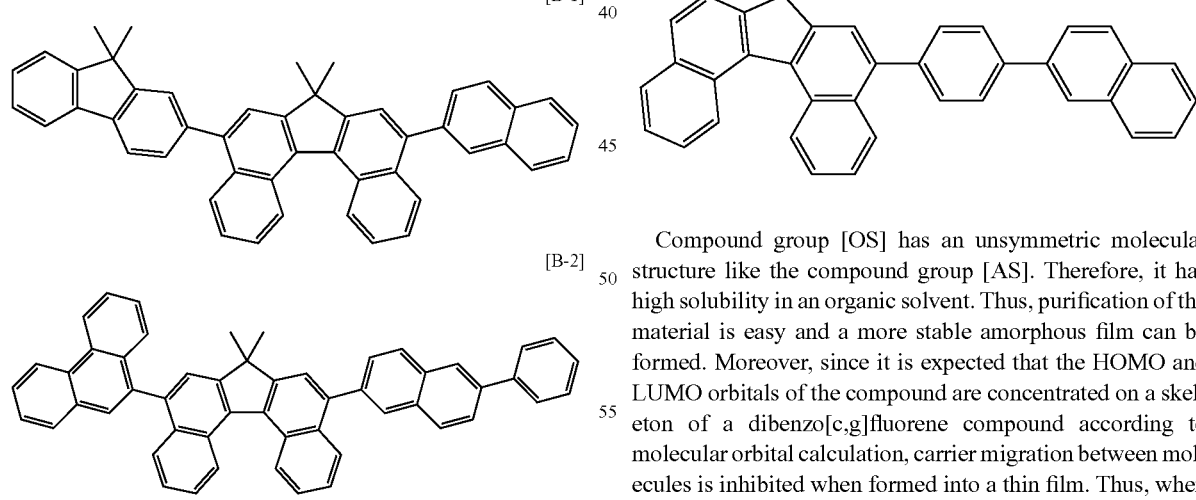

Having an unsymmetric molecular structure and low crystallinity, the compound group [AS] has high solubility in an organic solvent. Thus, purification of the material is easy and a more stable amorphous film can be formed.

(C) An aryl group is substituted only on 5-position of the skeleton of a dibenzo[c,g]fluorene compound. Herein below, it is designated as compound group [OS].

Compound group [OS]

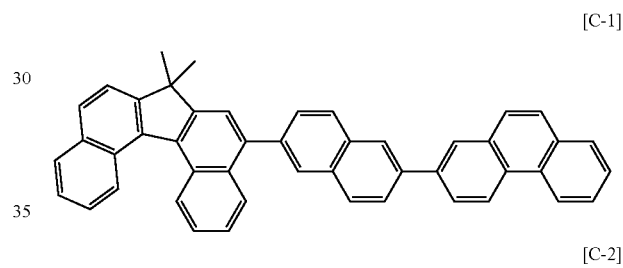

Compound group [OS] has an unsymmetric molecular structure like the compound group [AS]. Therefore, it has high solubility in an organic solvent. Thus, purification of the material is easy and a more stable amorphous film can be formed. Moreover, since it is expected that the HOMO and LUMO orbitals of the compound are concentrated on a skeleton of a dibenzo[c,g]fluorene compound according to molecular orbital calculation, carrier migration between molecules is inhibited when formed into a thin film. Thus, when the compound group [OS] is employed as a host for a light-emitting layer, carrier leakage from the light-emitting layer to a neighboring carrier transport layer is reduced so that a light emission region can be enlarged.

Herein below, specific structural formulae of the dibenzo [c,g]fluorene compound of the present invention are enumerated. However, these are only representative examples and the present invention is not limited thereto.

Compound Group [SY]
HA-01
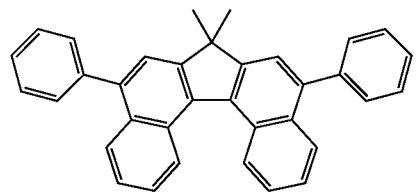
HA-02
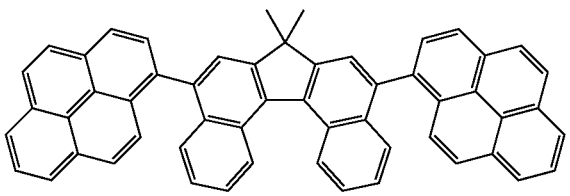
HA-03
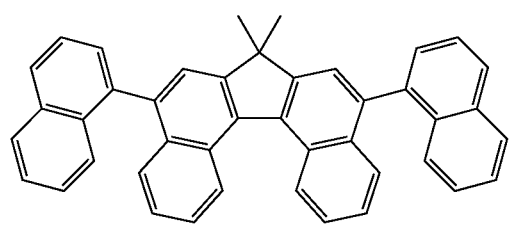
HA-04
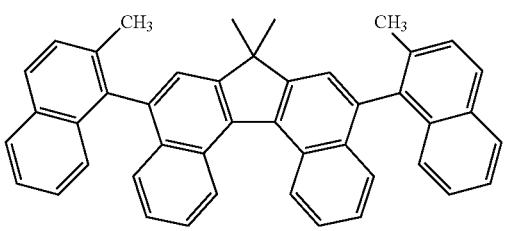
HA-05
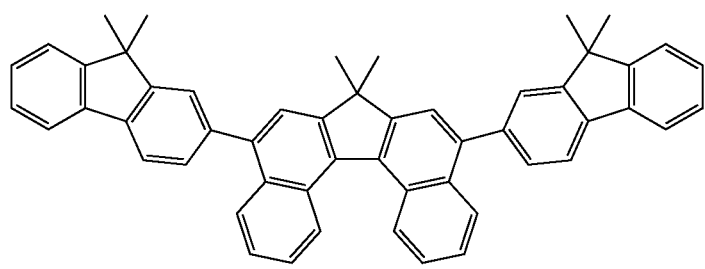
HA-06
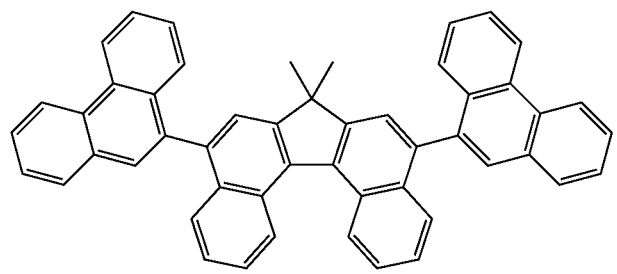
HA-07
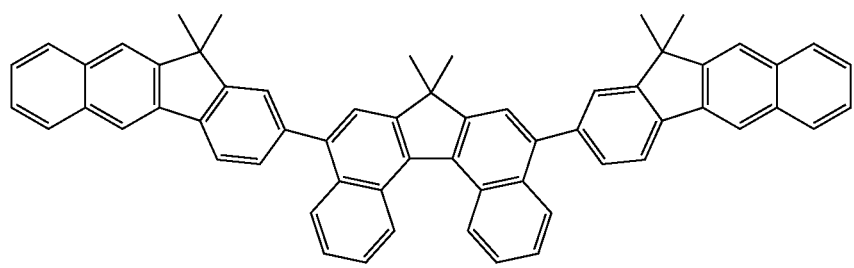
HA-08
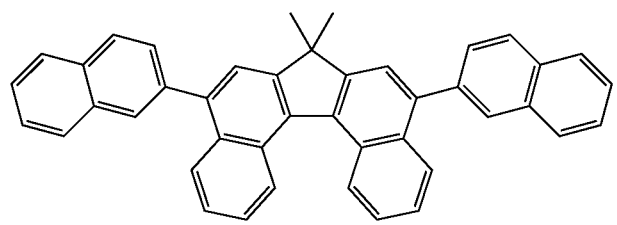

-continued
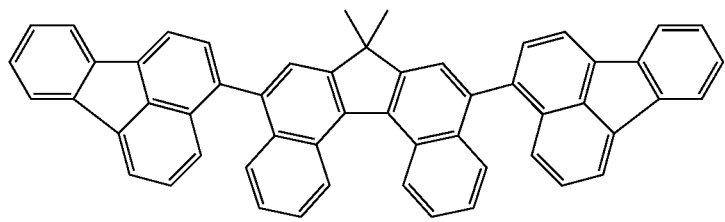
HA-09
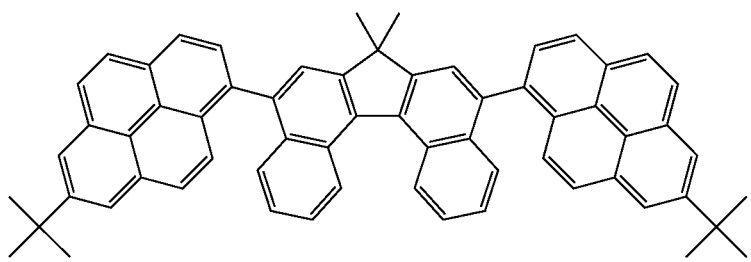
HA-10
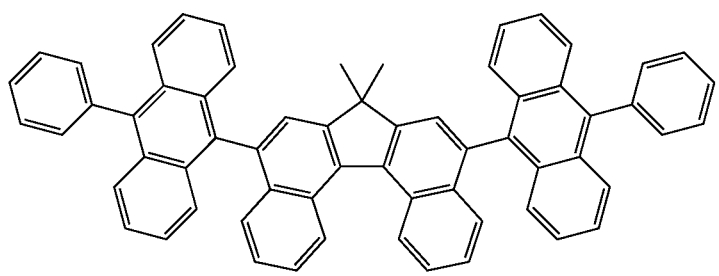
HA-11
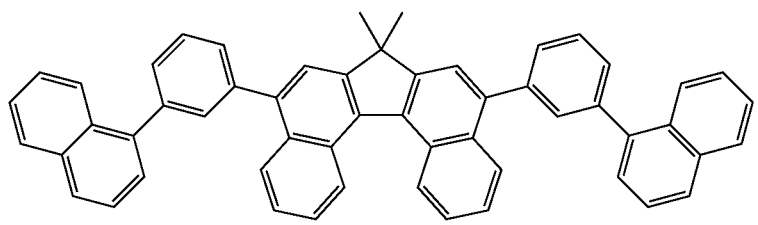
HA-12
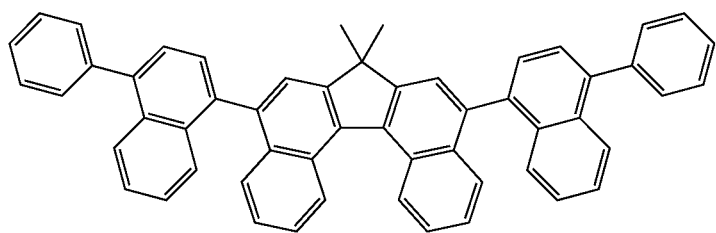
HA-13
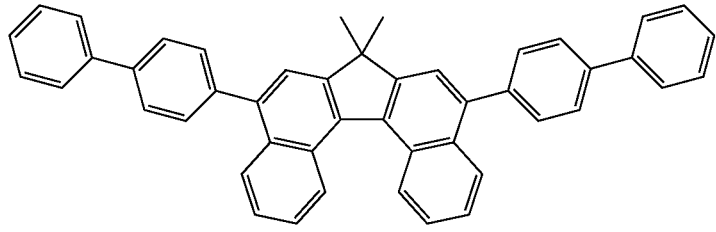
HA-14

-continued
HA-15
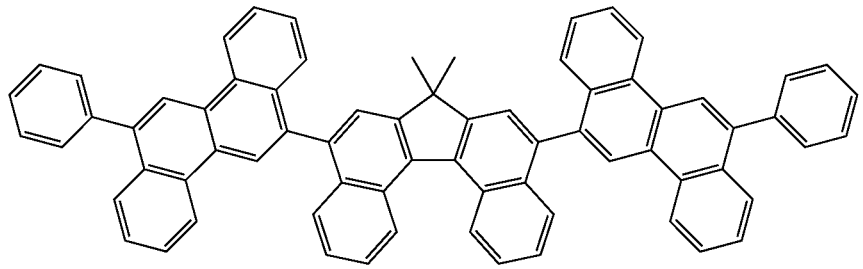
HA-16
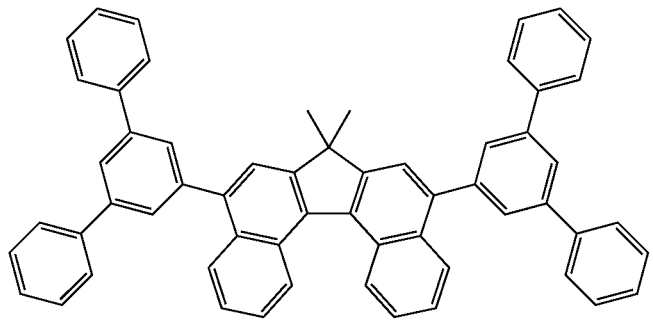
HA-17
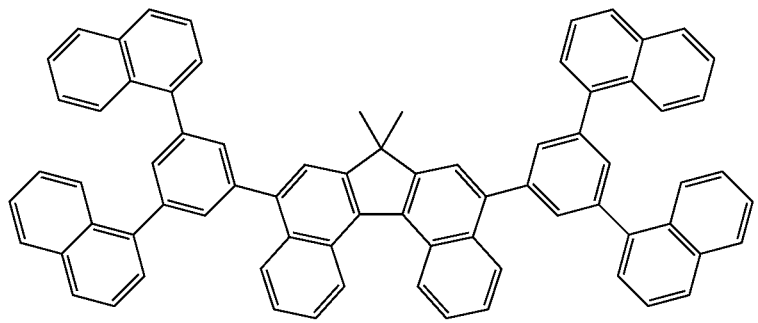
HA-18
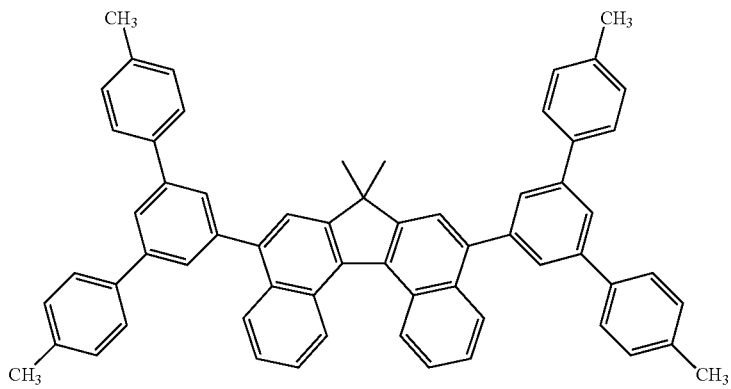
HA-19
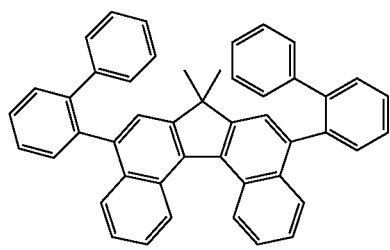
HA-20
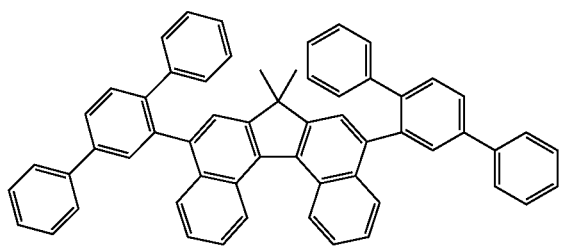

HA-21
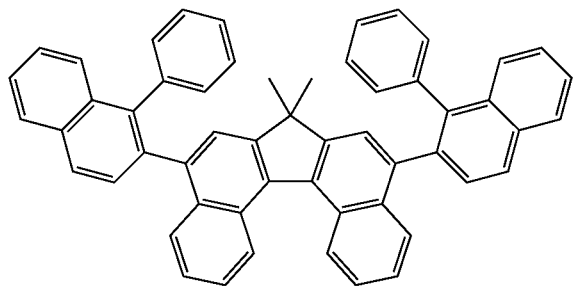
HA-22
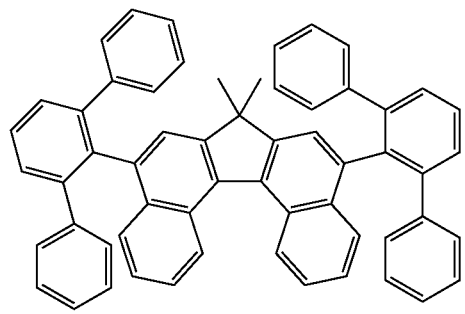
Compound Group [AS]
HA-23
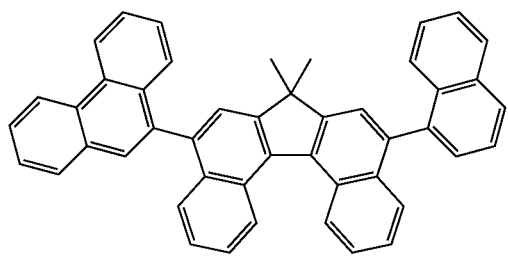
HA-24
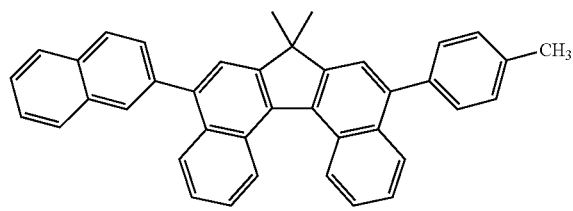
HA-25
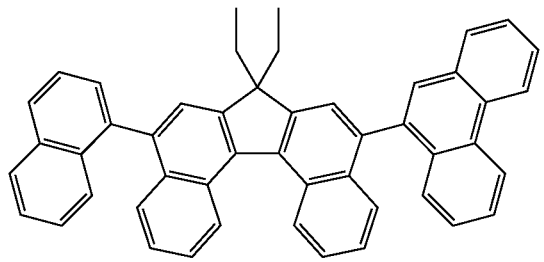
HA-26
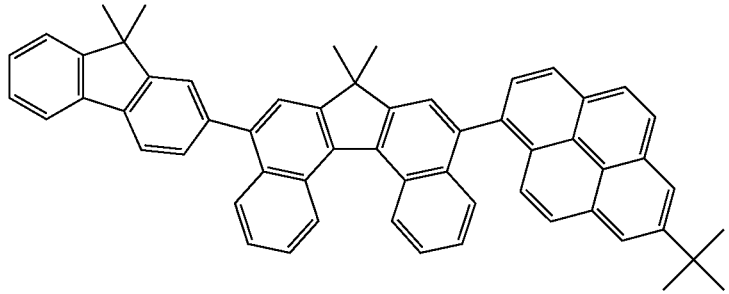
HA-27
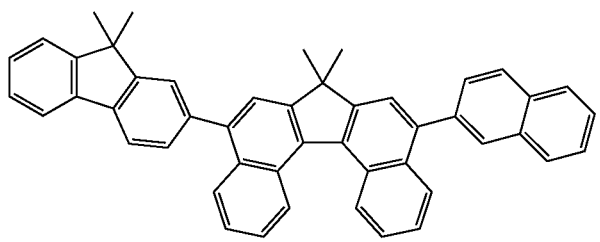
HA-28
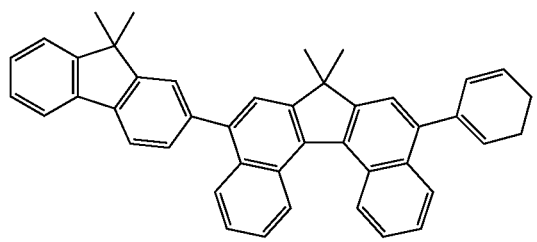

-continued
HA-29
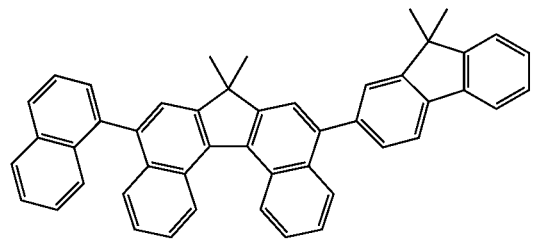
HA-30
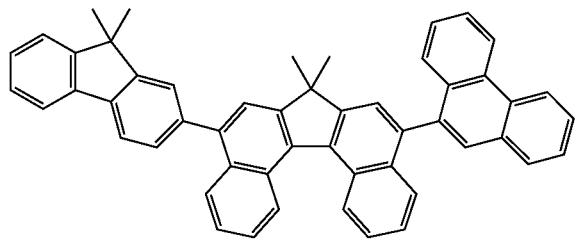
HA-31
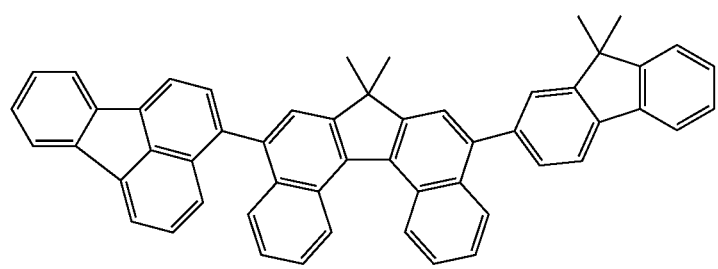
HA-32
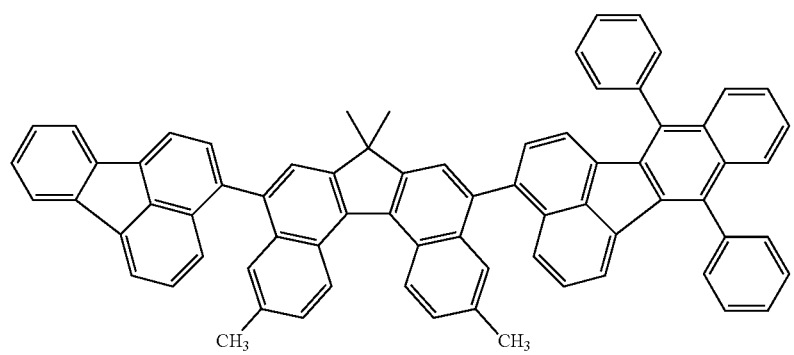
HA-33
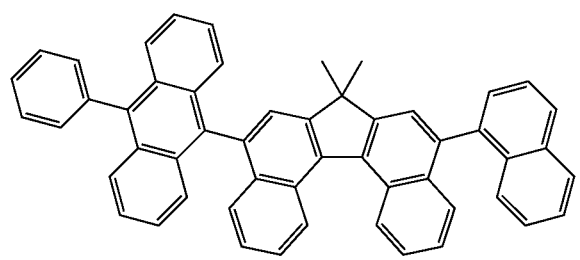
HA-34
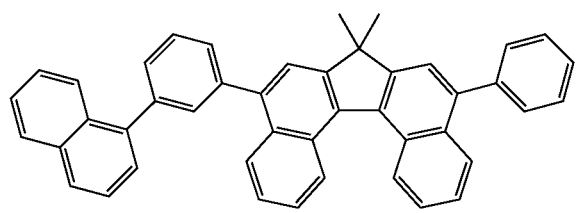
HA-35
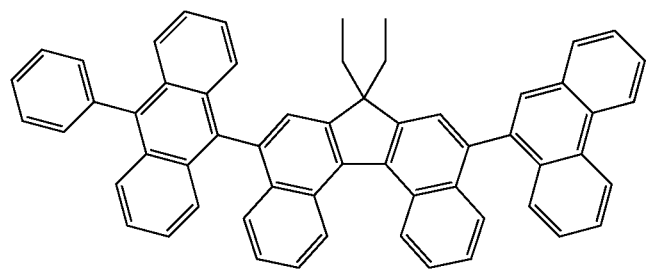

HA-36
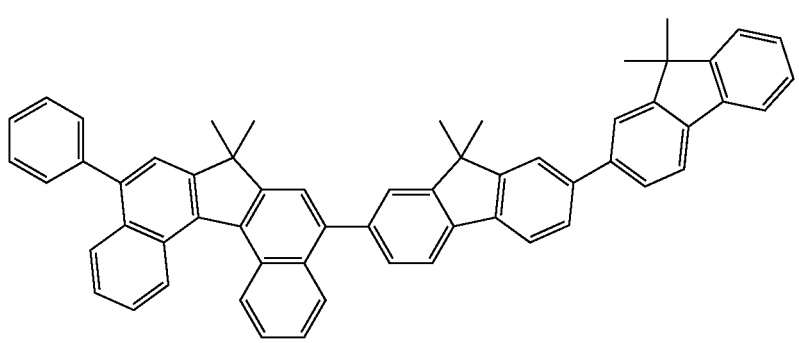
HA-37
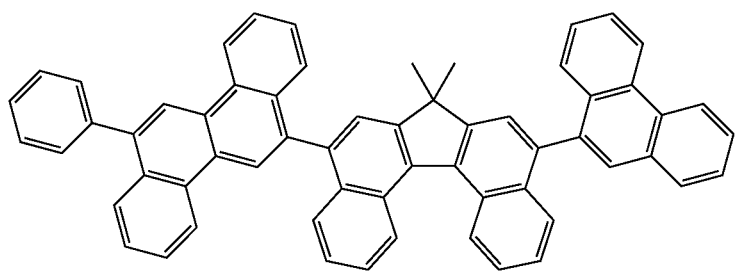
HA-38
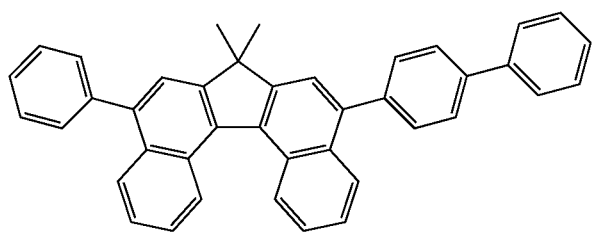
HA-39
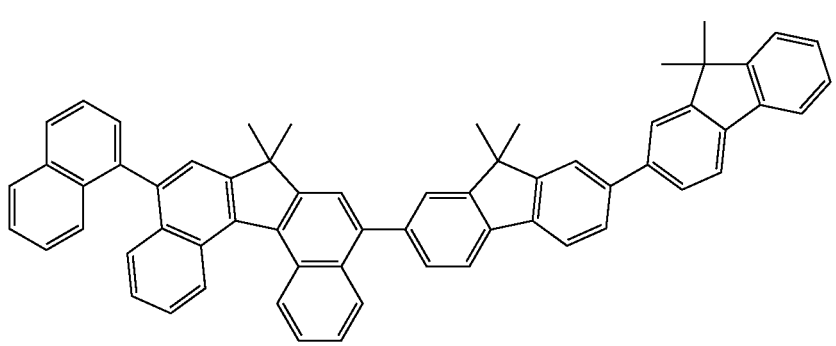
HA-41
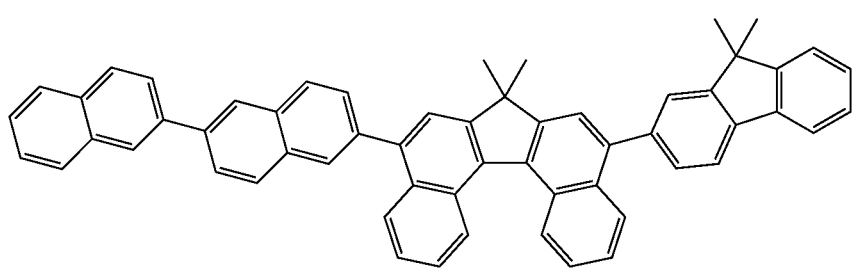

Compound Group [OS]
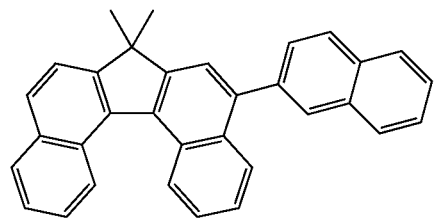
HB-01 … HB-10

-continued
HB-11
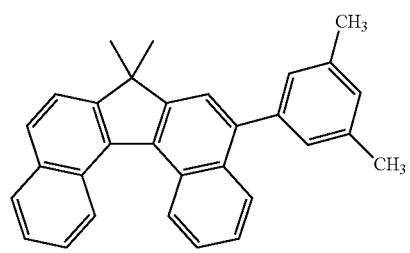
HB-12
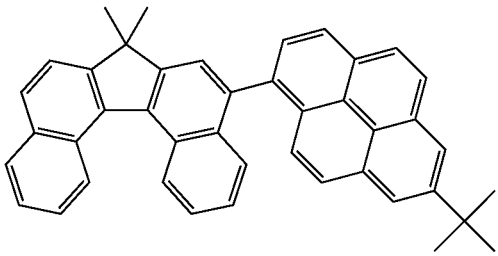
HB-13
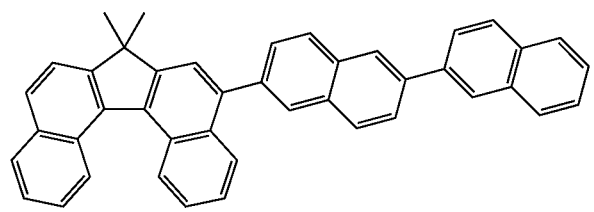
HB-14
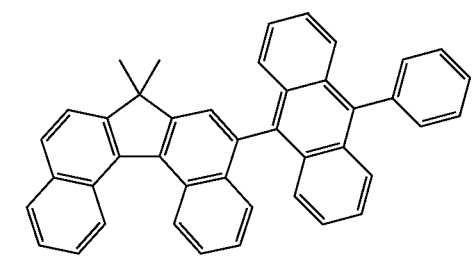
HB-15
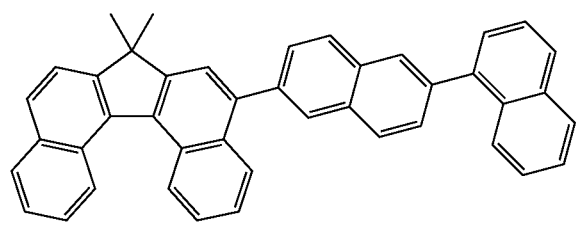
HB-16
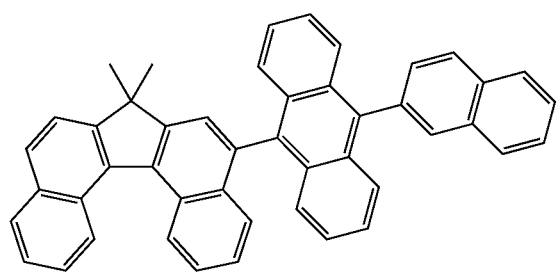
HB-17
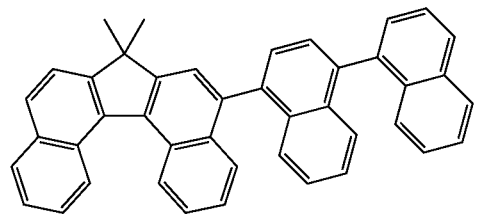
HB-18
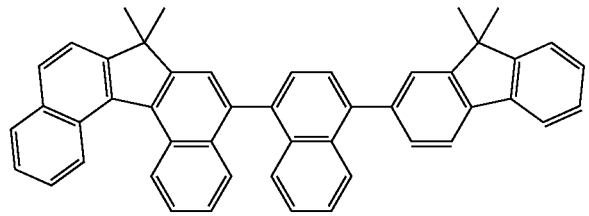
HB-19
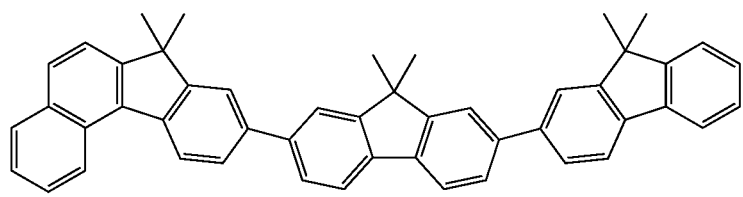
HB-20
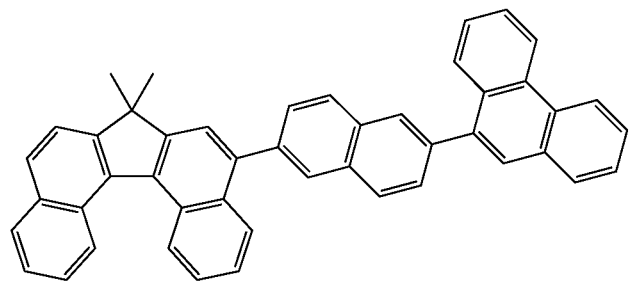

-continued
HB-21
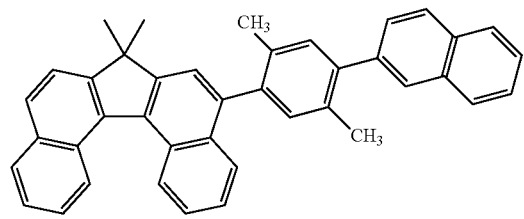
HB-22
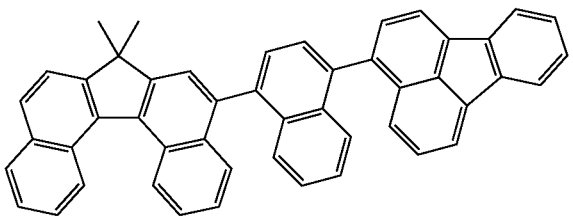
HB-23
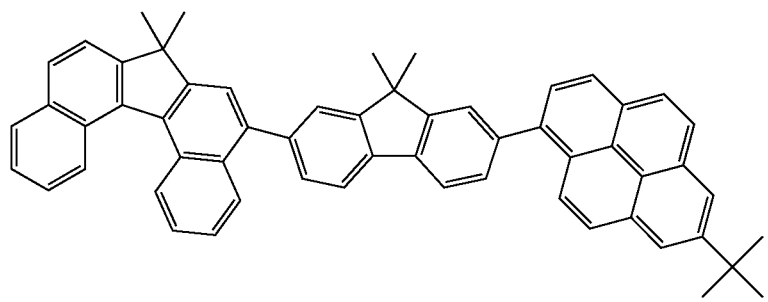
HB-24
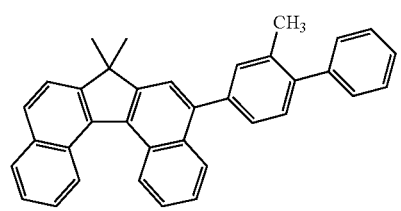
HB-25
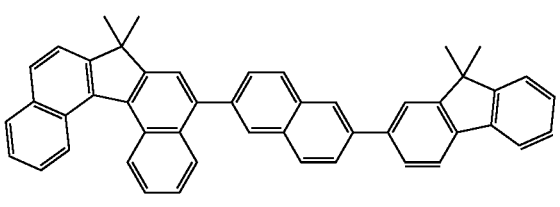
HB-26
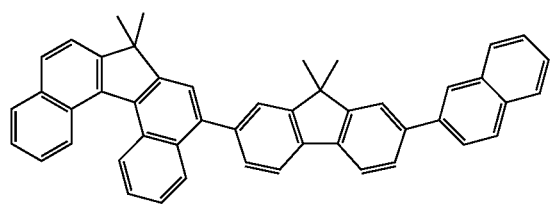
HB-27
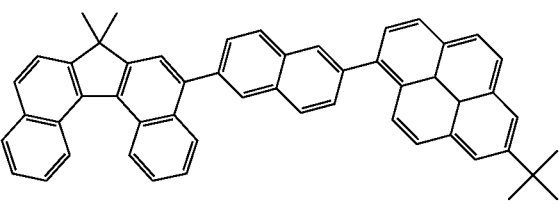
HB-28
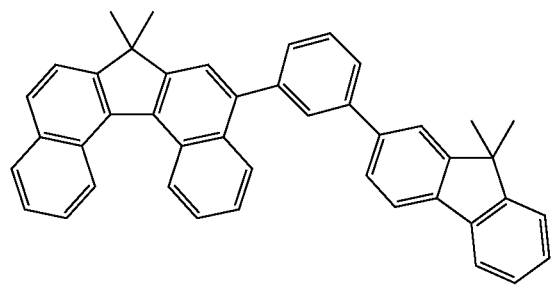
HB-29
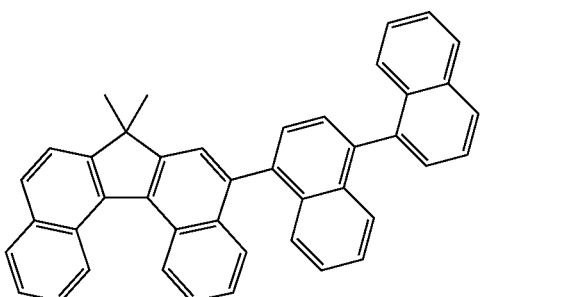
HB-30
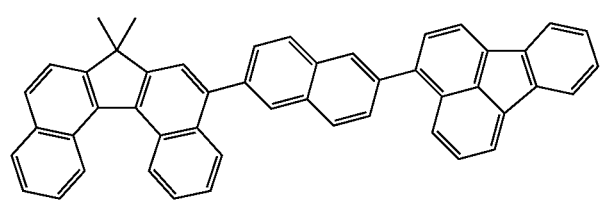
HB-31
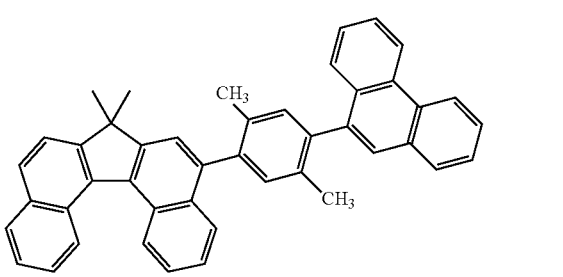

-continued
HB-32
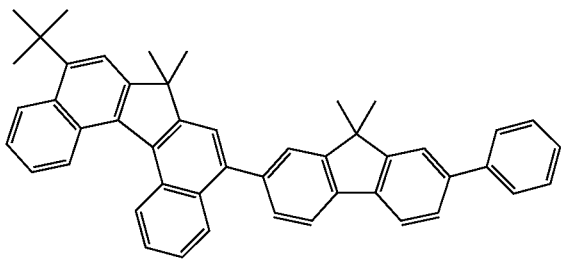
HB-33
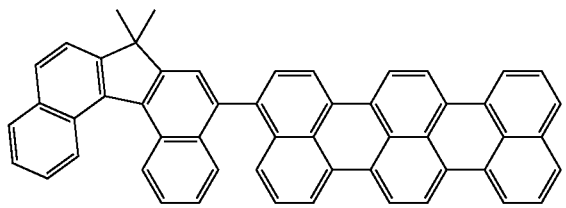
HB-34
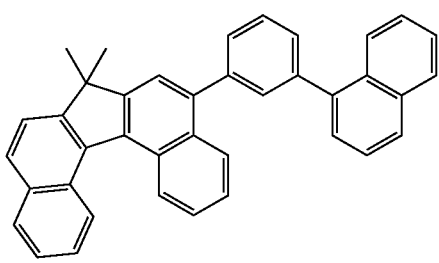
HB-35
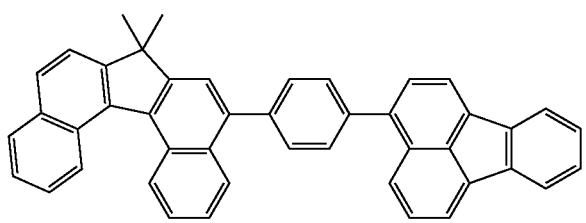
HB-36
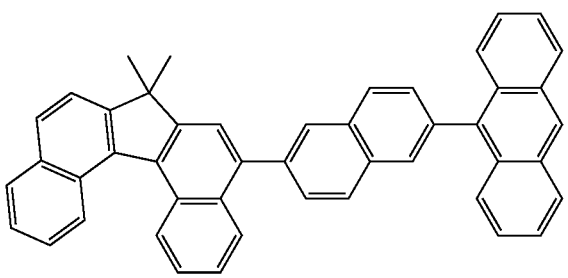
HB-37
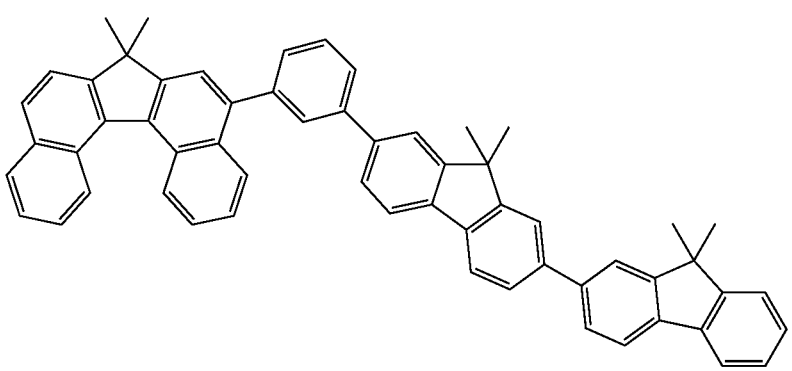
HB-38
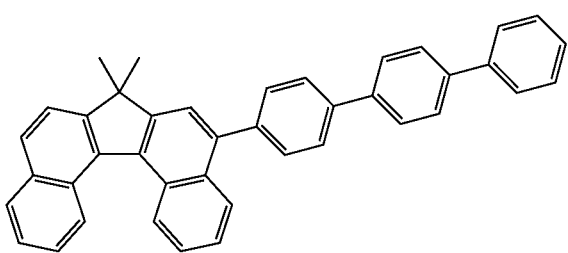
HB-39
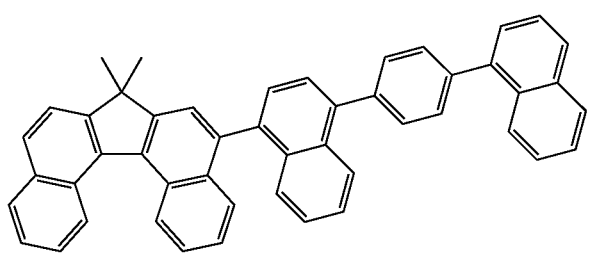

-continued
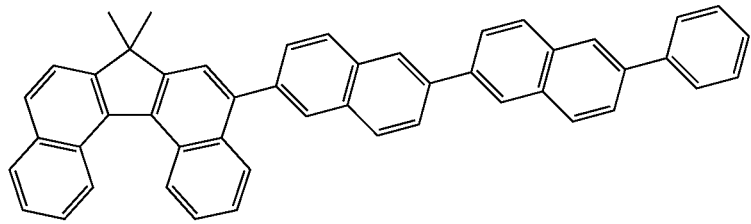
HB-40
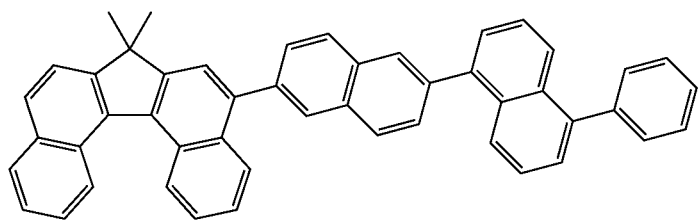
HB-41
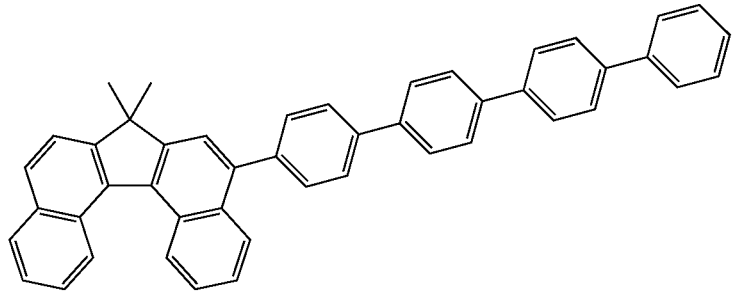
HB-42
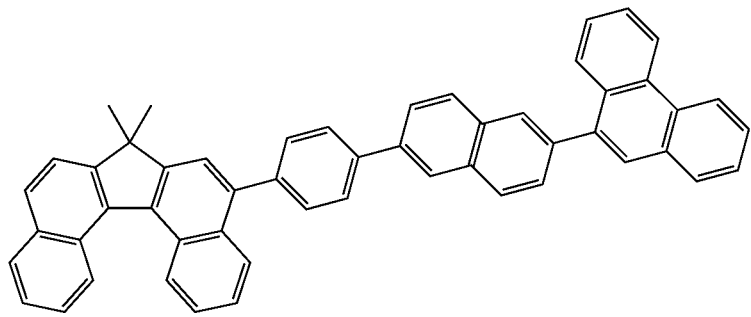
HB-43
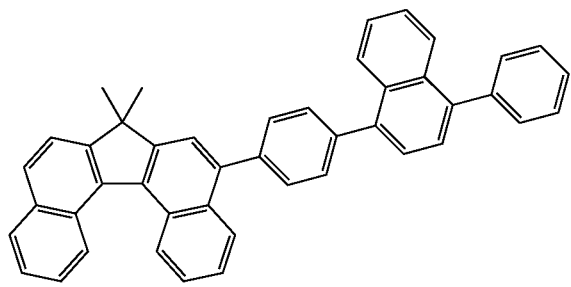
HB-44
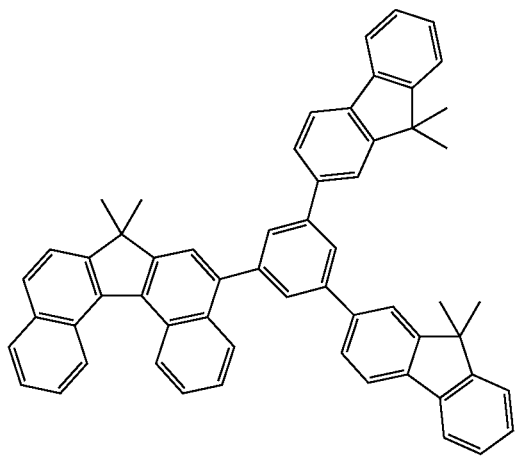
HB-45

HB-46

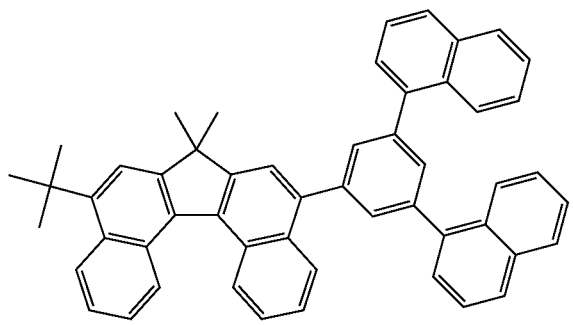

Next, the organic light-emitting device of the present invention will be described in detail.

The organic light-emitting device of the present invention is composed of an anode, a cathode and an organic compound layer which is interposed between the anode and the cathode.

Herein below, with reference to the drawings, the organic light-emitting device of the present invention is explained in detail.

First, symbols included in the drawings are explained. Reference numeral 1 denotes a substrate, reference numeral 2 denotes an anode, reference numeral 3 denotes an emission layer, reference numeral 4 denotes a cathode, reference numeral 5 denotes a hole transport layer, reference numeral 6 denotes an electron transport layer, reference numeral 7 denotes a hole injection layer, reference numeral 8 denotes a hole/exciton blocking layer, reference numeral 9 denotes an electron injection layer, and reference numerals 10, 20, 30, 40, 50 and 60 denote an organic light-emitting device.

Figure 2:
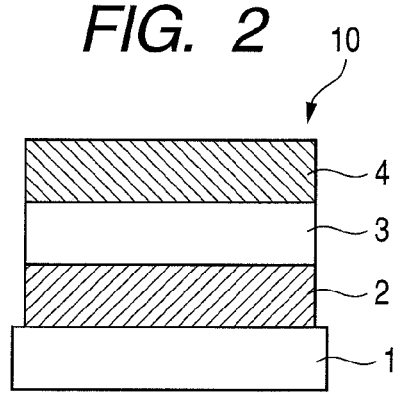
FIG. 2 is a cross-sectional view showing a first embodiment of an organic light-emitting device of the present invention.

FIG. 2 is a cross-sectional view showing a first embodiment of the organic light-emitting device of the present invention. In the organic light-emitting device 10 of FIG. 2, an anode 2, an emission layer 3 and a cathode 4 are sequentially formed on a substrate 1. This organic light-emitting device is useful when the emission layer 3 is composed of an organic compound which has hole transporting property, electron transporting property and light-emitting property all together. In addition, it is also useful even for the case in which a mixture containing organic compounds each having any one of hole transporting property, electron transporting property and light-emitting property is used.

Figure 3:
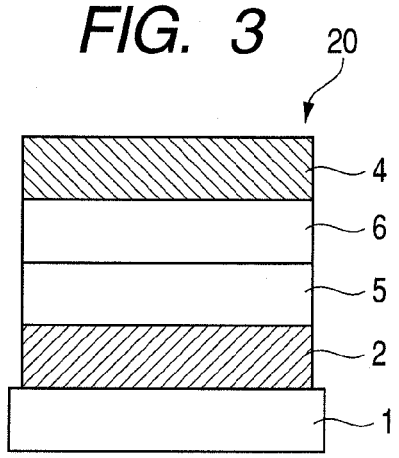
FIG. 3 is a cross-sectional view showing a second embodiment of an organic light-emitting device of the present invention.

FIG. 3 is a cross-sectional view showing a second embodiment of the organic light-emitting device of the present invention. In the organic light-emitting device 20 of FIG. 3, an anode 2, a hole transport layer 5, and an electron transport layer 6 and a cathode 4 are sequentially formed on a substrate 1. This organic light-emitting device 20 is useful when a light-emitting organic compound which has any one of hole transporting property and electron transporting property is used in combination with an organic compound which has either electron transporting property or hole transporting property. In addition, in this organic light-emitting device 20, the hole transport layer 5 or the electron transport layer 6 also serves as an emission layer.

Figure 4:
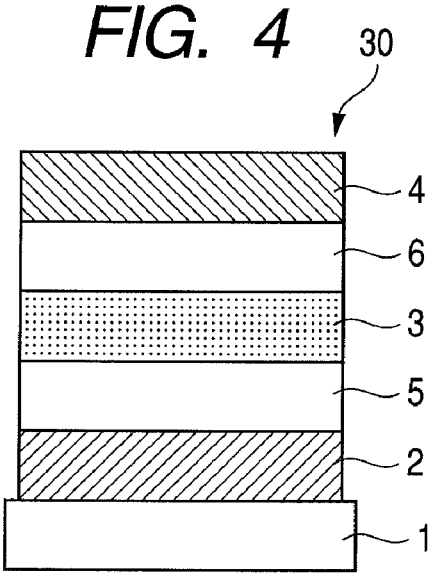
FIG. 4 is a cross-sectional view showing a third embodiment of an organic light-emitting device of the present invention.

FIG. 4 is a cross-sectional view showing a third embodiment of the organic light-emitting device of the present invention. In the organic light-emitting device 30 of FIG. 4, an emission layer 3 is additionally provided between the hole transport layer 5 and the electron transport layer 6 of the organic light-emitting device 20 of FIG. 3. In this organic light-emitting device 30, carrier transport and light emission are separated from each other, and it is used in an appropriate combination with organic compounds which have hole transporting property, electron transporting property and light-emitting property. Thus, the freedom in selecting the material is remarkably increased and at the same time various kinds of organic compounds having different emission wavelengths can be used, and diversification of the emission hue can be realized. Furthermore, with effective confinement of carriers or excitons within the emission layer 3 at a central region, the emission efficiency can be also improved.

Figure 5:
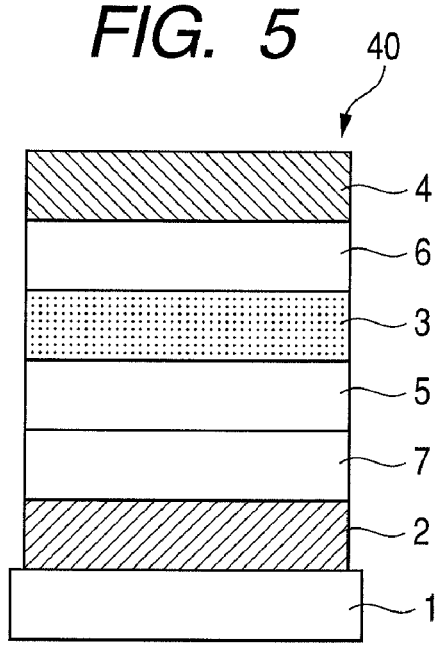
FIG. 5 is a cross-sectional view showing a fourth embodiment of an organic light-emitting device of the present invention.

FIG. 5 is a cross-sectional view showing the fourth embodiment of the organic light-emitting device of the present invention. In the organic light-emitting device 40 of FIG. 5, a hole injection layer 7 is additionally provided between the anode 2 and the hole transport layer 5 of the organic light-emitting device 30 of FIG. 4. By additionally providing the hole injection layer 7, the adhesiveness between the anode 2 and the hole transport layer 5 or the hole injectability is improved, and the drive voltage can be effectively lowered.

Figure 6:
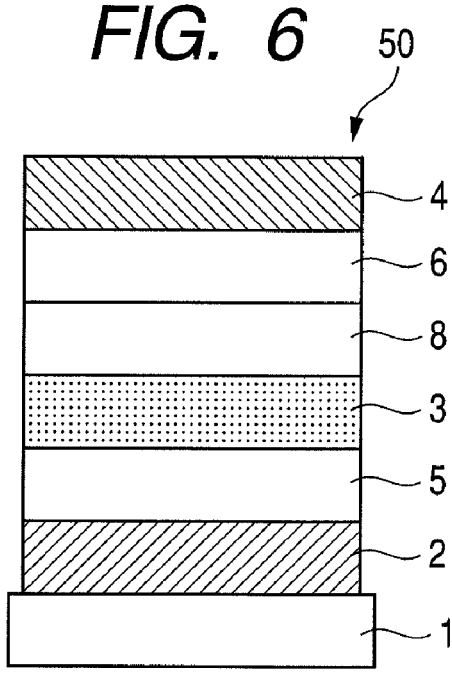
FIG. 6 is a cross-sectional view showing a fifth embodiment of an organic light-emitting device of the present invention.

FIG. 6 is a cross-sectional view showing a fifth embodiment of the organic light-emitting device of the present invention. In the organic light-emitting device 50 of FIG. 6, a layer (hole/exciton blocking layer 8) which inhibits leakage of holes or excitons to the cathode 4 side is additionally provided between the emission layer 3 and the electron transport layer 6 of the organic light-emitting device 30 of FIG. 4. When a material having a high ionization potential is used as a material which constitutes the hole/exciton blocking layer 8, the emission efficiency of a device can be effectively improved.

Figure 7:
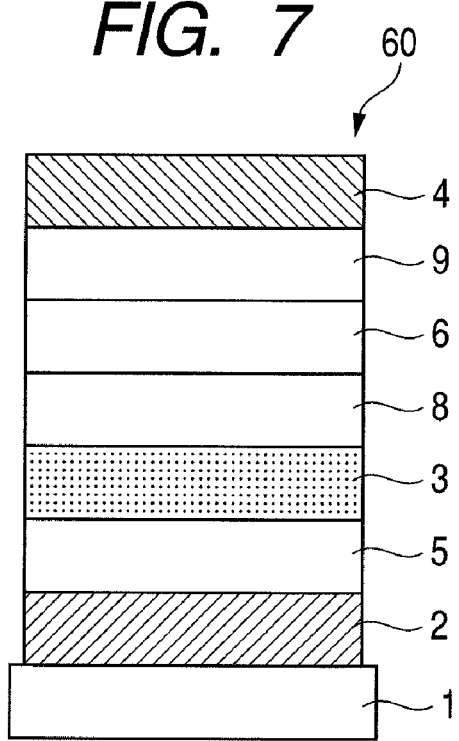
FIG. 7 is a cross-sectional view showing a sixth embodiment of an organic light-emitting device of the present invention.

FIG. 7 is a cross-sectional view showing a sixth embodiment of the organic light-emitting device of the present invention. In the organic light-emitting device 60 of FIG. 7, an electron injection layer 9 is additionally provided between the electron transport layer 6 and the cathode 4 of the organic light-emitting device 50 of FIG. 6.

However, the organic light-emitting devices shown in FIG. 2 to FIG. 7 represent devices having only basic configuration, and the configuration of the organic light-emitting device of the present invention is not limited thereto. For example, at an interface region between an electrode and an organic layer, an insulating layer, an adhesive layer or an interfering layer may be formed. Furthermore, various layer constitutions can be adopted, for example, a hole transport layer may be composed of two layers having different ionization potentials or an emission layer may have a stack structure having at least two layers and the like.

The dibenzo[c,g]fluorene compound of the present invention can be used for any one of the devices shown in FIG. 2 to FIG. 7. Specifically, at least one kind of the dibenzo[c,g]

fluorene compound of the present invention is contained in the organic compound layer which constitutes a device. In this case, the organic compound layer refers any one of the emission layer 3, the hole transport layer 5, the electron transport layer 6, the hole injection layer 7, the hole/exciton blocking layer 8 and the electron injection layer 9 shown in FIGS. 2 to 7. Preferably, it is the emission layer 3. When the dibenzo[c,g]fluorene compound is used as a constituent material of the emission layer 3, the emission efficiency of the organic light-emitting device is improved, light emission is maintained at a high luminance for a long period of time and energization degradation of the organic light-emitting device is reduced. Furthermore, a single kind or two or more kinds of the dibenzo[c,g]fluorene compound of the present invention can be included in a single layer.

Incidentally, although the emission layer 3 may consist of only the dibenzo[c,g]fluorene compound of the present invention, it is preferably composed of a host and a guest, and the host is the dibenzo[c,g]fluorene compound of the present invention.

The term "guest" herein employed refers to a compound which is responsible for main light emission in an emission layer. On the other hand, the term "host" herein employed refers to a compound which is present as a matrix around the guest in the emission layer. It is mainly responsible for transport of a carrier and supply of excitation energy to a guest.

In general, when an emission layer of an organic light-emitting device is composed of a host and a guest having a carrier transporting property, the main process for achieving light emission includes the following several steps.
(1) Transport of electrons/holes in emission layer
(2) Formation of excitons of host
(3) Excitation energy transfer between host molecules
(4) Excitation energy transport from host to guest The desired energy transport in the respective steps and light emission are caused through various deactivation processes and competitions.

In order to improve the emission efficiency of an organic light-emitting device, it is needless to say that the emission quantum yield of an emission center material itself needs to be increased. On the other hand, making an improvement in efficiency of energy transport between a host and a host or between a host and a guest is also a large issue. Furthermore, although the reason for degradation in light emission due to energization, which causes reduction in emission efficiency of an organic light-emitting device, has not been identified at the present, at least it is assumed that it is caused by an environmental change in the light-emitting material by a emission center material itself or by neighboring molecules.

Incidentally, the dibenzo[c,g]fluorene compound of the present invention has the following characteristics.
1. An ionic impurity which becomes a carrier trap is difficult to be incorporated.
2. HOMO is appropriately shallow, and carrier balance is improved.
3. When used in an emission layer, an exciplex is hardly formed.
4. Film property with favorable steric hindrance is provided.

Based on the above characteristics, when the dibenzo[c,g]fluorene compound of the present invention is used as a material for constituting an organic light-emitting device, a high efficiency and a longer lifetime of a device can be achieved.

Although it is preferable that the dibenzo[c,g]fluorene compound of the present invention is used as a material for constituting the emission layer 3 as described above, it can be also used as a material for constituting a carrier transport layer (hole transport layer 5, electron transport layer 6, hole injection layer 7 and electron injection layer 9). For example, among the compounds exemplified in the above, a compound having a high electron mobility can be used as a material for constituting the electron transport layer 6 or the electron injection layer 9.

The dibenzo[c,g]fluorene compound of the present invention is effectively used as a host or a guest of the emission layer 3 of an organic light-emitting device.

With respect to an organic light-emitting device of the present invention, when the dibenzo[c,g]fluorene compound of the invention is used as a host of an emission layer, generally known fluorescent compound and phosphorescent compound can be used as a guest, with the fluorescent compound being preferred. In this case, for attaining emission of lights of a plurality of colors from the emission layer 3 or for aiding transfer of excitons or electrons, a plurality of kinds of fluorescent compounds can be introduced into the emission layer 3.

Here, the concentration of a guest with respect to a host is 0.01 wt % to 50 wt %, preferably 1 wt % to 30 wt % based on the total weight of the material which constitutes the emission layer 3.

Furthermore, the guest may be uniformly distributed throughout the entire emission layer 3. Alternatively, it may be distributed so as to have a concentration gradient. Still further, the guest may be contained only in a limited region of the emission layer 3 such that a region which contains no guest is formed in the emission layer 3.

As described above, the organic light-emitting device of the present invention utilizes the dibenzo[c,g]fluorene compound of the present invention particularly as a material which constitutes an emission layer. However, if necessary, a known low molecular weight or high molecular weight hole transporting compound, light-emitting compound, electron transporting compound or the like may be used in combination therewith.

Herein below, examples of such compounds are described.

As the hole transporting (injecting) compound, a material having a high hole mobility is preferably used for facilitating the injection of holes from the anode 2 and transporting the injected holes to the emission layer 3. Examples of a low molecular weight material and a high molecular weight material each having a hole injecting/transporting property include, but are not limited to, a triarylamine derivative, a phenylenediamine derivative, a stilbene derivative, a phthalocyanine derivative, a porphyrin derivative, poly (vinylcarbazole), poly (thiophene), and other conductive polymers.

As the light-emitting compound which is mainly involved in the light-emitting function of a device, examples include, but are not limited to, in addition to the dibenzofluorene compound of the present invention, a fused ring compound (for example, a fluorene derivative, a pyrene derivative, a tetracene derivative, 9,10-diphenylanthracene derivative, a rubrene derivative and the like), a quinacridone derivative, a coumarine derivative, a stilbene derivative, an organoaluminium complex such as tris(8-quinolinolato) aluminium, and a high molecular weight derivative such as poly(phenylenevinylene) derivative, poly(fluorene) derivative, and poly (phenylene) derivative.

The electron transporting (injecting) compound can be arbitrarily selected from those compounds which can facilitate the injection of electrons from the cathode 4 and can transport the injected electrons to the emission layer 3 in consideration of a balance with the carrier mobility of the hole transporting material or the like. Examples of the material having electron transporting (injecting) property include, but are not limited to, an oxadiazole derivative, an oxazole derivative, a pyrazine derivative, a triazole derivative, a triazine derivative, a quinoline derivative, a quinoxaline derivative, a phenanthroline derivative, and an organoaluminium complex.

As the material which constitutes the anode 2, those having as large a work function as possible are preferred. Examples thereof include metal elements such as gold, platinum, silver, copper, nickel, palladium, cobalt, selenium, vanadium, and tungsten, or alloys of these metal elements and metal oxides such as tin oxide, zinc oxide, indium oxide, indium tin oxide (ITO), and indium zinc oxide. A conductive polymer such as polyaniline, polypyrrole, polythiophene and the like can also be used. Each of those electrode substances can be used alone, or two or more of them can be used in combination. In addition, the anode 2 may be constituted of a single layer, or may be constituted of a plurality of layers.

On the other hand, the material for the cathode 4 desirably has a smaller work function. Examples thereof include an elemental metal including an alkaline metal such as lithium, an alkaline earth metal such as calcium, and other metals such as aluminium, titanium, manganese, silver, lead, and chromium. Furthermore, alloys including two or more of these metal elements can be also used. Examples thereof include a magnesium-silver alloy, an aluminium-lithium alloy, an aluminium-magnesium alloy and the like. A metal oxide such as indium tin oxide (ITO) can be also used. Each of those electrode substances can be used alone, or two or more of them can be used in combination. In addition, the cathode may be constituted of a single layer, or may be constituted of a plurality of layers.

The substrate 1 used in the organic light-emitting device of the present invention is not particularly limited, but an opaque substrate such as a metal substrate, and a ceramic substrate or a transparent substrate such as glass, quartz, and a plastic sheet can be used. In addition, a color filter film, a fluorescent color conversion filter film, a dielectric reflection film and the like can be used for the substrate to control the emitted light.

Incidentally, the produced device may be provided with a protective layer or an encapsulating layer for the purpose of preventing the device from contacting oxygen or moisture, and the like, for example. Examples of the protective layer include a diamond thin film, an inorganic material film made of, for example, a metal oxide or a metal nitride, a polymer film such as fluororesin, polyethylene, silicone resin, or polystyrene resin, and a photocurable resin and the like. In addition, the device may be covered with glass, a gas impermeable film, a metal, or the like, and the device itself can be packaged with an appropriate encapsulating resin.

It is also possible to make a thin film transistor (TFT) on a substrate and produce the organic light-emitting device of the present invention so as to be connected thereto.

In addition, with regard to the direction of extracting light from the device, both a bottom emission configuration (i.e., a configuration in which light is extracted from a substrate side) and a top emission configuration (i.e., a configuration in which light is extracted from the side opposite to the substrate side) are available.

For the organic light-emitting device of the present invention, a layer containing the dibenzofluorene compound of the present invention and layers containing other organic compounds may be formed by any one of the various processes described below. In general, a thin film is formed by a vacuum evaporation process, an ionization-assisted evaporation process, a sputtering process, or a plasma process, or by dissolving a film material in an appropriate solvent and subjecting the solution to a known application method (such as a spin coating process, a dipping process, a casting process, an LB process, or an ink jet process). In this case, when a layer is formed by a vacuum evaporation process or by a solution coating process, crystallization and the like hardly occurs and the stability over time is excellent. Furthermore, when a film is formed by the coating method, a film may be formed by additionally using an appropriate binder resin.

Examples of the binder resin include, but are not limited to, a polyvinyl carbazole resin, a polycarbonate resin, a polyester resin, an ABS resin, an acrylic resin, a polyimide resin, a phenol resin, an epoxy resin, a silicone resin, a urea resin and the like. Furthermore, these binder resins may be either a homopolymer or a copolymer. Furthermore, they can be used alone or in combination of two or more. Still furthermore, if required, a known additive such as a plasticizer, an antioxidant, and a UV absorber may be used in combination with the binder resin.

EXAMPLES

Herein below, the present invention will be described more specifically by way of Examples. However, the present invention is not limited to these Examples.

Example 1

Synthesis of Exemplified Compound HB-25

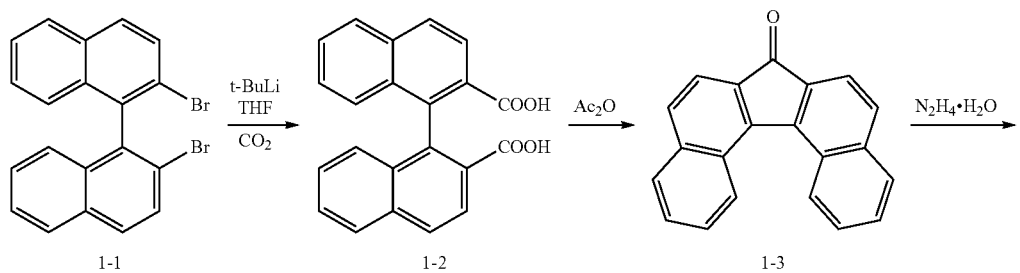

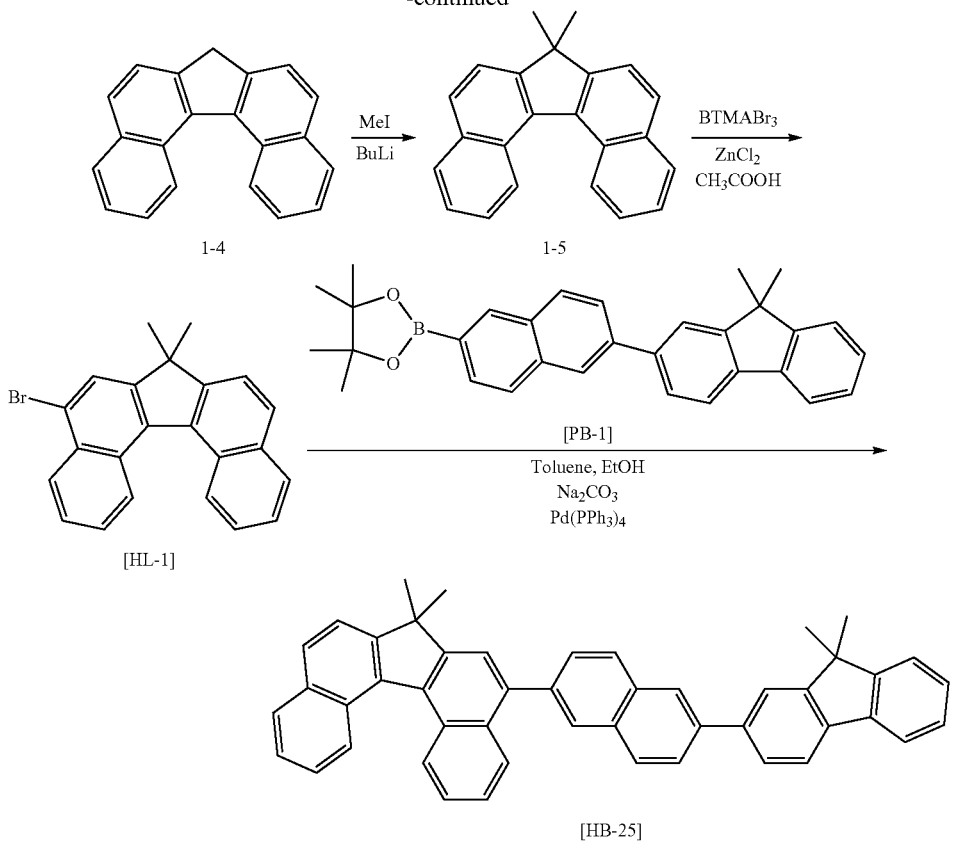

(1) Synthesis of Compound 1-2
The following reagent and solvent were placed In a reaction vessel.
Compound 1-1: 80 g (194.1 mmol)
anhydrous THF: 800 ml
Next, the reaction solution was cooled to −78° C. and the inside atmosphere of the reaction vessel was replaced with an argon gas atmosphere. After adding dropwise tert-BuLi, the reaction solution was stirred for 1 hour while being maintained at −78° C. Next, after carbon dioxide gas was bubbled into the reaction solution, the solution was warmed to room temperature and then stirred for 20 hours. After the completion of the reaction, 10% HCl was added to acidify the reaction solution followed by extraction of an organic layer with chloroform. Then, the organic layer was dried over anhydrous sodium sulfate, and the solvent was evaporated under reduced pressure, whereby a crude product was obtained. The thus obtained crude product was purified by recrystallization with chloroform to give 44 g of Compound 1-2 (yield: 66%).

(2) Synthesis of Compound 1-3
The following reagent and solvent were placed in a reaction vessel.
Compound 1-2: 35 g (102.2 mmol)
anhydrous acetic acid: 350 ml
Next, the reaction solution was heated to 140° C. and then stirred for one hour at the same temperature. Then, the reaction solution was concentrated under reduced pressure to obtain a residue, which was then collected by filtration and heated at 300° C. for 3 hours. After cooling, the residues were purified by recrystallization with toluene to give 4.0 g of Compound 1-3. In addition, the filtrate which had been obtained at the time of the filtration of the residue as described above was further concentrated under reduced pressure to give a crude product. The thus obtained crude product was purified by column chromatography (gel for chromatography: PSQ100 (trade name; manufactured by FUJI SILYSIA CHEMICAL LTD.; developing solvent: hexane/ethyl acetate=5/1) to give 5.0 g of Compound 1-3. Thus, taken all together, 9.0 g of Compound 1-3 was obtained (yield: 32%).

(3) Synthesis of Compound 1-4
The following reagent and solvent were placed in a sealed tube.
Compound 1-3: 9.0 g (32.1 mmol)
hydrazine: 54 ml
Next, the above tube was completely sealed and heated to 180° C., followed by stirring for 15 hours. After cooling, an obtained crystal were filtered and washed with methanol to give 6.4 g of Compound 1-4 (yield: 75%).
With an analysis based on MALDI-TOF MS (Matrix Assisted Ionization—Time of Flight Mass Spectroscopy), 280.7 as M⁺ of Compound 1-4 was confirmed.

(4) Synthesis of Compound 1-5
The following reagents and solvent were placed in a reaction vessel.
Compound 1-4: 6.4 g (24.0 mmol)
methyl iodide: 6.9 g (48 mmol)
potassium iodide: 438 mg (2.63 mmol)
anhydrous DMSO: 100 ml
Next, the reaction solution was cooled in an ice bath and the inside atmosphere of the reaction vessel was replaced with an argon gas atmosphere. The, after adding 5.7 g (101.6 mmol) of potassium hydroxide, the reaction solution was stirred for 15 minutes. Then, after the reaction solution was warmed to room temperature, it was stirred for 15 hours. Next, after 2.3 g (16 mmol) of methyl iodide was added, the reaction solution was heated to 60° C. followed by stirring at this temperature for 7 hours. Next, after the reaction solution was cooled, an organic layer was extracted with ethyl acetate. Next, after the organic layer was dried over anhydrous sodium sulfate, the solvent was evaporated under reduced pressure, whereby a crude product was obtained. The thus obtained crude product was purified by column chromatography (gel for chromatography: PSQ60 (trade name; manufactured by FUJI SILYSIACHEMICAL LTD.; developing solvent: hexane) to give 4.4 g of Compound 1-5 (yield: 62%).

With an analysis based on MALDI-TOF MS (Matrix Assisted Ionization—Time of Flight Mass Spectroscopy), 294.8 as $M^+$ of Compound 1-5 was confirmed.

(5) Synthesis of Compound [HL-1]

The following reagent and solvent were placed in a light-shielded vessel.

Compound 1-5: 4.1 g (11.0 mmol)
chloroform: 600 ml

Next, while the reaction solution was cooled in an ice bath, 4.29 g (11.0 mmol) of benzyltrimethyl ammonium tribromide ($BTMABr_3$) was added thereto. Thereafter, the reaction vessel was sealed, followed by stirring for 30 minutes. After the completion of the reaction, water was added and an organic layer was extracted with chloroform. Next, the organic phase was dried over anhydrous sodium sulfate, and the solvent was evaporated under reduced pressure, whereby a crude product was obtained. The thus obtained crude product was purified by column chromatography (gel for chromatography: PSQ60 (trade name; manufactured by FUJI SILYSIA CHEMICAL LTD.; developing solvent: hexane) to give 3.0 g of Compound [HL-1] (yield: 73%).

With an analysis based on MALDI-TOF MS (Matrix Assisted Ionization—Time of Flight Mass Spectroscopy), 373.7 as $M^+$ of Compound [HL-1] was confirmed.

(6) Synthesis of Exemplified compound HB-25

The following reagents and solvents were placed in a reaction vessel.

Compound [HL-1]: 0.30 g (0.80 mmol)
Compound [PB-1]: 0.36 g (0.81 mmol)
toluene: 10 ml
ethanol: 5 ml
2N aqueous sodium carbonate solution: 10 ml Next, while the reaction solution was stirred at room temperature under nitrogen atmosphere, 0.040 g (0.035 mmol) of tetrakis(triphenylphosphine)palladium (0) was added thereto. Subsequently, after the reaction solution was heated to 75° C., it was stirred for 40 hours. After the completion of the reaction, water was added to the reaction solution and the organic phase was extracted with toluene. Next, the organic phase was dried over anhydrous sodium sulfate, the solvent was evaporated under reduced pressure, whereby a crude product was obtained. The thus obtained crude product was purified by column chromatography (gel for chromatography: BW300 (trade name; manufactured by FUJI SILYSIA CHEMICAL LTD.; developing solvent: toluene/heptane=¼). Furthermore, according to recrystallization by using a toluene/heptane mixed solvent, 0.36 g of Exemplified compound HB-25 was obtained (yield: 73%).

With an analysis based on MALDI-TOF MS (Matrix Assisted Ionization—Time of Flight Mass Spectroscopy), 678.9 as $M^+$ of Compound HB-25 was confirmed.

In addition, with $^1$H-NMR measurement (600 MHz, $CDCl_3$), the structure of the compound was identified.

σ (ppm):8.82-8.81 (d, 1H), 8.78-8.77 (d, 1H), 8.24 (s, 1H), 8.13-8.09 (m, 3H), 8.06-8.04 (d, 1H), 8.02-8.00 (d, 1H), 7.96-7.95 (d, 1H), 7.93-7.92 (dd, 1H), 7.88-7.85 (m, 2H), 7.82-7.79 (m, 3H), 7.77 (s, 1H), 7.72-7.71 (d, 1H), 7.62-7.60 (m, 2H), 7.56-7.54 (t, 1H), 7.51-7.47 (m, 2H), 7.41-7.35 (m, 2H), 1.65 (s, 6H), 1.61 (s, 6H)

Furthermore, as a result of measurement using a photoelectron spectroscope AC-2 (manufactured by Riken Keiki Co., LTD), the HOMO value was found to be 5.69 eV. Still further, according to the bandgap determined with a ultraviolet-visible spectrophotometer, the LUMO value was found to be 2.80 eV.

Comparative Example 1

Synthesis of Comparative Compound N-1

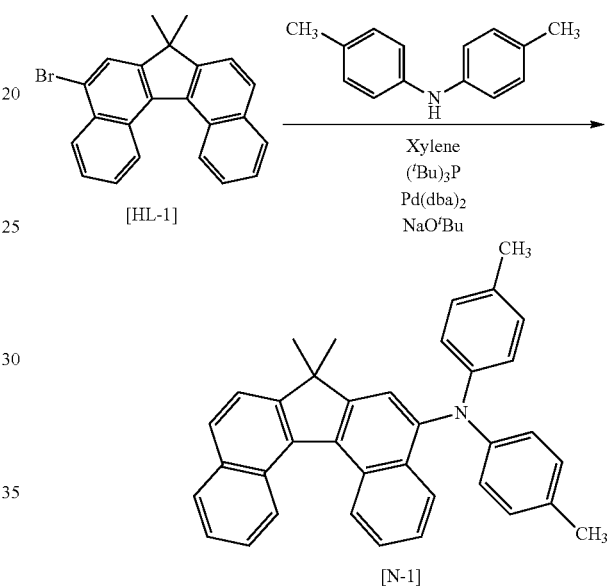

The following reagents and solvent were placed in a reaction vessel.

Compound [HL-1]: 0.30 g (0.80 mmol)
p,p'-ditolyl amine: 0.14 g (0.72 mmol)
xylene: 10 ml Next, while the reaction solution was stirred at room temperature under nitrogen atmosphere, the following reagents were added sequentially thereto.
bis(dibenzylidene acetone) palladium (0): 0.092 g (0.16 mmol)
sodium tert-butoxide: 0.31 g (3.21 mmol)
tri-tert-butyl phosphine: 0.13 g (0.64 mmol)

Next, the reaction solution was heated to 135° C. and stirred for 24 hours at the same temperature. After the completion of the reaction, water was added and the organic phase was extracted with toluene. Next, the organic phase was dried over anhydrous sodium sulfate, and the solvent was evaporated under reduced pressure, whereby a crude product was obtained. The thus obtained crude product was purified by column chromatography (gel for chromatography: BW300 (trade name; manufactured by FUJI SILYSIA CHEMICAL LTD.; developing solvent: toluene/heptane=½) followed by recrystallization with ethanol to give 0.20 go of Comparative Compound N-1 (yield: 51%).

With an analysis based on MALDI-TOF MS (Matrix Assisted Ionization—Time of Flight Mass Spectroscopy), 489.7 as $M^+$ of Compound N-1 was confirmed.

Furthermore, as a result of measurement using a photoelectron spectroscope AC-2 (manufactured by Riken Keiki Co., LTD), the HOMO value was found to be 5.53 eV. Still further, according to a bandgap determined with a ultraviolet-visible spectrophotometer, the LUMO value was found to be 2.87 eV.

Examples 2 to 4

Exemplified Compounds HB-13, HB-18 and HB-19 are synthesized by following the same procedure as in Example 1 with the exception that the boronic acid ester derivatives shown in the following Table 9 are used instead of Compound [PB-1] used in Example 1(6). Incidentally, each of the measured values of HOMO is obtained by using a photoelectron spectroscope AC-2 (manufactured by Riken Keiki Co., LTD) and each of the measured values of LUMO is obtained from a bandgap determined with a ultraviolet-visible spectrophotometer.

TABLE 9

| | Boronic acid ester derivative | HOMO [eV] | LUMO [eV] |
|---|---|---|---|
| Example 2 Exemplified Compound HB-13 | | 5.74 | 2.82 |
| Example 3 Exemplified Compound HB-18 | | 5.72 | 2.72 |
| Example 4 Exemplified Compound HB-19 | | 5.67 | 2.79 |

Example 5

Synthesis of Exemplified Compound HA-19

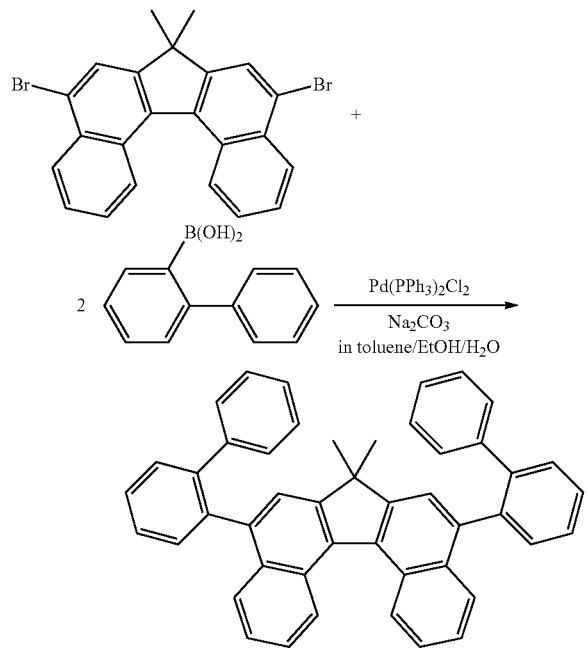

After the inside atmosphere of a 100 mL recovery flask was replaced with a nitrogen gas atmosphere, the following reagents and solvents were added thereto.
7,7'-diemthyl-5,8-dibromodibenzo[c,g]fluorene: 0.60 g (1.33 mmol)
2-biphenyl boronic acid: 0.55 g (2.78 mmol)
toluene: 20 ml
ethanol: 10 ml Next, after adding 10 mL of a 10 wt % of an aqueous sodium carbonate solution, the reaction solution was stirred at room temperature for 30 minutes. Then, after adding 55 mg (0.078 mmol) of bis(triphenylphosphine)palladium (II) dichloride thereto, the reaction solution was stirred for 4 hours under heating and reflux. Upon the completion of the reaction, the organic layer was extracted with toluene, washed with water, and dried over anhydrous sodium sulfate. By concentrating the organic layer under reduced pressure, a crude product was obtained. Next, the thus obtained crude product was subjected to silica gel column chromatography (developing solvent: heptane/toluene=4/1). Subsequently, slurry washing under heating with a heptane/toluene mixed solvent and slurry washing under heating with an ethanol/chloroform mixed solvent were carried out sequentially followed by vacuum drying under heating at 130° C. to give 610 mg of Exemplified Compound HA-19 (yield: 77%).

Identification of the thus obtained compound was carried out. Results are described below.
[MALDI-TOF MS (Matrix Assisted Ionization—Time of Flight Mass Spectroscopy)]
Found value: m/z=598.15; calculated value: $C_{47}H_{34}$=598.27
[$^1$H-NMR (400 MHz, $CDCl_3$)]
δ:8.69 (t, 2H), 7.90 (t, 2H), 7.65-7.45 (m, 10H), 7.42-7.38 (m, 2H), 7.22 (s, 1H), 7.16 (s, 1H), 7.11-6.95 (m, 10H), 1.35 (s, 1.5H), 1.06 (s, 3H), 0.87 (s, 1.5H)

Example 6

Manufacture of Organic Light-Emitting Device

An organic light-emitting device having the configuration shown in FIG. 4 was produced by the following procedure.

On a glass plate (substrate 1), indium tin oxide (ITO) film was formed by use of a sputtering process to form an anode 2. At this time, thickness of the anode 2 was 120 nm. Next, the resulting was subjected to ultrasonic cleaning with acetone and isopropyl alcohol (IPA) sequentially, then washed with boiled IPA, and dried. Next, the substrate was subjected to UV/ozone cleaning. The thus treated substrate was used as a transparent conductive support substrate.

Next, by use of a vacuum evaporation process, Compound A represented by the following formula was formed into a film on the anode 2 to form a hole transport layer 5. At this time, the thickness of the hole transport layer 5 was 30 nm. In addition, the degree of vacuum was $1.0 \times 10^{-4}$ Pa at the time of the evaporation and the film formation rate was 0.1 nm/sec.

Compound A

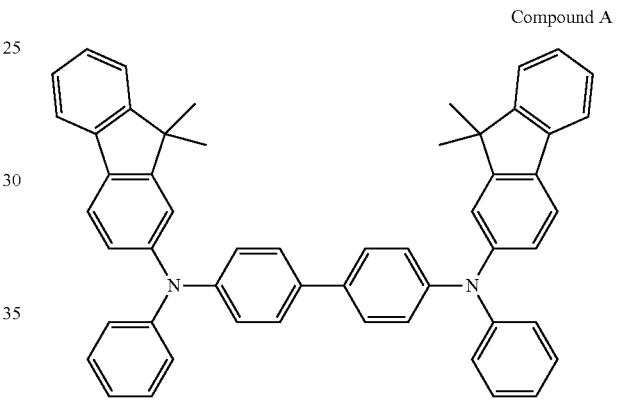

Next, by use of a vacuum evaporation method, Exemplified Compound HB-25 as a host and Compound B as a guest represented by the following formula were co-evaporated on the hole transport layer 5 such that the content of Compound B was 5 wt % with respect to the total weight of the emission layer 3, thereby forming an emission layer 3. At this time, the thickness of the emission layer 3 was 50 nm. In addition, the degree of vacuum was $1.0 \times 10^4$ Pa at the time of the evaporation and the film formation rate was 0.1 nm/sec.

Compound B

Next, by use of a vacuum evaporation process, Compound C represented by the following formula was formed into a film on the emission layer 3 to form an electron transport layer 6. At this time, thickness of the electron transport layer 6 was 40 nm. In addition, the degree of vacuum was $1.0 \times 10^{-4}$ Pa at the time of the evaporation and the film formation rate was 0.2 nm/sec to 0.3 nm/sec.

Compound C

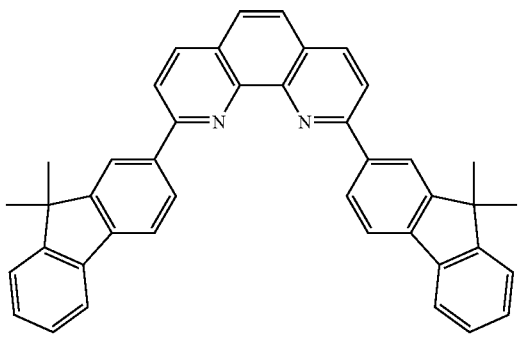

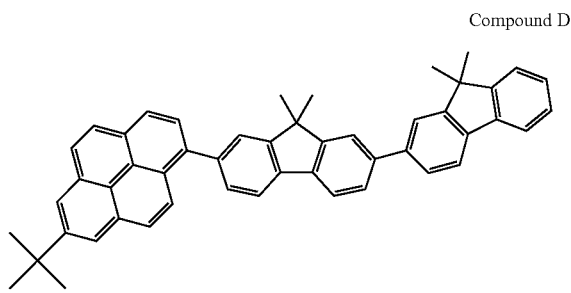 [SMILES: CC(C)(C)c1cc2ccc3ccc(-c4ccc5c(c4)C(C)(C)c4cc(-c6ccc7c(c6)C(C)(C)c6ccccc6-7)ccc4-5)c4ccc(c1)c2c34]

Compound D

Next, by use of a vacuum evaporation process, a lithium fluoride film was formed on the electron transport layer 6. At this time, the thickness of the lithium fluoride film was 0.5 nm. Then, by use of a vacuum evaporation process, an aluminium film was formed on the lithium fluoride film. At this time, the thickness of the aluminium film was 150 nm. Incidentally, for the formation of the lithium fluoride film and the aluminium film, the degree of vacuum was $1.0 \times 10^{-4}$ Pa at the time of the evaporation and the film formation rate was 1.0 nm/sec to 1.2 nm/sec. In this case, both the lithium fluoride film and the aluminium film (aluminium-potassium alloy film) function as an electron injection electrode (cathode 4).

Next, in order to prevent degradation of the organic light-emitting device by moisture adsorption, the device was covered with a protective glass plate in a dry air atmosphere, and then encapsulated with an acrylic resin adhesive. By the above described procedure, the organic light-emitting device was obtained.

When a voltage of 4.8 V was applied to the thus obtained organic light-emitting device with the ITO electrode (anode 2) being connected to a positive electrode of a power supply and the Al electrode (cathode 4) being connected to a negative electrode of the power supply, emission of blue light (CIE chromaticity coordinates: x=0.14, y=0.20) at an emission efficiency of 6.5 cd/A was observed. Furthermore, when the device was subjected to endurance driving while flowing a constant current of 100 mA/cm² therein, the luminance reduction ratio compared to the initial luminance was 19% after the elapse of 100 hours.

An organic light-emitting device having the configuration shown in FIG. 4 is produced by following the same procedure as in Example 6 with the exception that Exemplified Compound HB-25 is used instead of Compound B as the guest for the emission layer 3 and Compound D represented by the following formula is used instead of Exemplified Compound HB-25 as the host for the emission layer 3.

Comparative Example 2

An organic light-emitting device was produced by following the same procedure as in Example 6 with the exception that Comparative Compound N-1 was used instead of Exemplified Compound HB-25 as the host for the emission layer 3. Evaluation of the device was performed in the same manner as in Example 6 with the result that the luminance reduction ratio compared to the initial luminance was 48% after the elapse of 100 hours.

As described above, the organic light-emitting device using the dibenzo[c,g]fluorene compound of the present invention provides light emission with a high efficiency and a high luminance. In addition, the organic light-emitting device of the present invention is excellent in durability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-127889, filed May 15, 2008, which is hereby incorporated by reference herein in its entirety.

The invention claimed is:

1. A dibenzo[c,g]fluorene compound represented by General Formula (1):

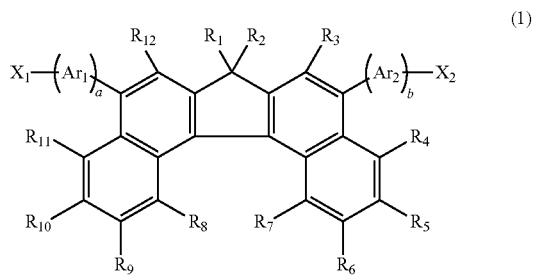

wherein, $X_1$ and $X_2$ each represent a hydrogen atom, a substituted or unsubstituted aryl group, or a substituted or unsubstituted alkyl group and may be the same or different, $Ar_1$ and $Ar_2$ each represent a substituted or unsubstituted arylene group and may be the same or different, $R_1$, $R_2$, $R_3$, $R_4$, $R_5$, $R_6$, $R_7$, $R_8$, $R_9$, $R_{10}$, $R_{11}$, and $R_{12}$ each represent a hydrogen atom, a substituted or unsubstituted alkyl group and may be the same or different, and a and b each represent an integer of 0 to 3, provided that a +b is 1 or more and 4 or less, and when a is 2 or more, $Ar_1$'s may be the same or different and when b is 2 or more, $Ar_2$'s may be the same or different.

2. The dibenzo[c,g]fluorene compound according to claim 1, wherein a is 0 and $X_1$ is a hydrogen atom or a substituted or unsubstituted alkyl group.

3. The dibenzo[c,g]fluorene compound according to claim 1, wherein $Ar_2$ is selected from a group consisting of a substituted or unsubstituted phenylene group, a substituted or unsubstituted biphenylene group, a substituted or unsubstituted terphenylene group, a substituted or unsubstituted naphthylene group, a substituted or unsubstituted anthrylene group, a substituted or unsubstituted phenanthrylene group, a substituted or unsubstituted pyrenylene group and a substituted or unsubstituted fluorenylene group.

4. An organic light-emitting device comprising:
an anode and a cathode; and
an organic compound layer which is interposed between the anode and the cathode,
wherein the organic compound layer comprises at least one dibenzo[c,g]fluorene compound set forth in claim 1.

5. The organic light-emitting device according to claim 4, wherein the dibenzo[c,g]fluorene compound is contained in a light-emitting layer.

6. The organic light-emitting device according to claim 5, wherein the light-emitting layer comprises a host and a guest, and the host is the dibenzo[c,g]fluorene compound.

* * * * *